(12) United States Patent
Chen

(10) Patent No.: US 8,945,918 B2
(45) Date of Patent: Feb. 3, 2015

(54) EXPRESSION IN INSECT CELLS OF GENES WITH OVERLAPPING OPEN READING FRAMES, METHODS AND COMPOSITIONS THEREFOR

(75) Inventor: Haifeng Chen, Castro Valley, CA (US)

(73) Assignee: Virovek, Inc., Hayward, CA (US)

( * ) Notice: Subject to any disclaimer, the term of this patent is extended or adjusted under 35 U.S.C. 154(b) by 1143 days.

(21) Appl. No.: 12/297,958

(22) PCT Filed: Aug. 24, 2007

(86) PCT No.: PCT/US2007/076799
§ 371 (c)(1),
(2), (4) Date: Oct. 28, 2008

(87) PCT Pub. No.: WO2008/024998
PCT Pub. Date: Feb. 28, 2008

(65) Prior Publication Data
US 2009/0203071 A1 Aug. 13, 2009

Related U.S. Application Data

(60) Provisional application No. 60/839,761, filed on Aug. 24, 2006.

(51) Int. Cl.
*C12N 15/00* (2006.01)
*C12N 15/85* (2006.01)
*C12N 7/00* (2006.01)
*C07K 14/005* (2006.01)

(52) U.S. Cl.
CPC *C12N 15/85* (2013.01); *C12N 7/00* (2013.01); *C12N 2750/14151* (2013.01); *C12N 2800/105* (2013.01); *C12N 2800/50* (2013.01); *C12N 2840/20* (2013.01); *C07K 14/005* (2013.01)
USPC .................................................... 435/320.1

(58) Field of Classification Search
CPC . A61K 2039/505; A61K 38/00; C07K 16/20; C07K 14/47; C07K 14/705
USPC .................................................... 435/320.1
See application file for complete search history.

(56) References Cited

U.S. PATENT DOCUMENTS

| | | | |
|---|---|---|---|
| 5,688,676 A | 11/1997 | Zhou et al. | |
| 5,691,176 A | 11/1997 | Lebkowski et al. | |
| 5,741,683 A | 4/1998 | Zhou et al. | |
| 6,156,303 A | 12/2000 | Russell et al. | |
| 6,204,059 B1 | 3/2001 | Samulski et al. | |
| 6,541,258 B2 | 4/2003 | Allen et al. | |
| 7,271,002 B2 * | 9/2007 | Kotin et al. | 435/456 |
| 2001/0016355 A1 | 8/2001 | Samulski et al. | |
| 2004/0197866 A1 * | 10/2004 | Johnson et al. | 435/69.1 |
| 2004/0197895 A1 | 10/2004 | Kotin et al. | |
| 2009/0191597 A1 | 7/2009 | Samulski et al. | |

FOREIGN PATENT DOCUMENTS

| | | |
|---|---|---|
| WO | 96/17947 | 6/1996 |
| WO | 00/24916 | 5/2000 |
| WO | 00/47757 | 8/2000 |
| WO | WO 03/042361 * | 5/2003 |
| WO | 2007084773 | 7/2007 |

OTHER PUBLICATIONS

Beutler et al., 199, J. Clin. Invest. 87: 1336-1344.*
Trempe et al., 1988, Journal of Virology, 62: 3356-3363.*
Jeang et al., 1987, Journal of Virology, 61: 1761-1764.*
Supplementary European Search Report issued on Jun. 26, 2010 in connection with EP 07614439, priority to PCT Application No. PCT/US07/76799.
Cao, L., et al., Journal of Virology, 74: 11456-11463, 2000.
Chen, H., et al., The American Society of Gene Therapy, 161 924-930, 2008.
Qiao, C., et al., Journal of Virology, 76: 13015-13027, 2002.
Urabe, M., et al., Human Gene Therapy, 13: 1935-1943, 2002.
An et al, J. Gen. Virol., 1999, 80:1009-1016.
Bantel-Schaal et al, J. Virol., 1999, 73:939-947.
Berns, Parvoviridae: The Viruses and Their Replication, 3d Ed. 1996, Chapter 69 in Fields Virology.
Brown et al, J. Virol., 1991, 65:2702-2706.
Chang et al, J. Gen. Virol., 1997, 78:1435-1439.
Chiorini J. et al, J. Virol., 1997, 71:6823-6833.
Chiorini J. et al, J. Virol., 1999, 73:1309-1319.
Chiorini J. et al, J. Virol., 1999, 73:4293-4298.
Conway, J. et al, Gene Thereapy, 1999, 6:986-993.
Conway, J. et al, J. Virol., 1997, 71:8780-8789.
Davidson et al, Proc. Natl. Acad. Sci. USA, 2000, 97:3428-3432.
Ding, C. et al, J. Virol., 2002, 76:338-345.
Gao, G. et al, Human Gene Therapy, 1998, 9:2353-2362.
Grimm et al, Hum. Gene Ther., 1999, 10:2445-2450.
Hoque, M. et al, J. Biochem. & Biophys., 1999, 266:371-376.
Jennings et al, Arthritis Res, 2001, 3:1, abstract.
King, J. et al, Embo J., 2001, 20:3282-3291.
Kosukegawa et al, Biochim. Biophys. Acta, 1996, 1290:37-45.

(Continued)

*Primary Examiner* — Anoop Singh
*Assistant Examiner* — David A Montanari
(74) *Attorney, Agent, or Firm* — Ann-Louise Kerner; DLA Piper LLP US

(57) ABSTRACT

The present teachings disclose nucleic acid cassettes for expressing in an insect cell a plurality of polypeptides encoded by a gene comprising overlapping open reading frames (ORFs). A cassette comprises, in 5' to 3' order, a) a first insect cell-operable promoter, b) a 5' portion of a gene comprising a first ORF of the gene, c) an intron comprising a second insect cell-operable promoter, and d) a 3' portion of the gene comprising at least one additional ORF. Vectors and insect cells comprising the cassettes are also disclosed, as well as methods for production of recombinant adeno-associated virus in insect cells using the cassettes.

26 Claims, 14 Drawing Sheets

(56) References Cited

OTHER PUBLICATIONS

McCarty, D. et al, J. Virol., 1994, 68:4988-4997.
Montross et al, J. Virol., 1991, 65:4991-4998.
Owens, R., Virology, 1991, 184:14-22.
Palombo, F. et al, J. Virol., 1998, 72:5025-5034.
Qiao, C., et al, J. Virol., 2002, 76:1904-1913.
Ruffing, M. et al, J. Virol., 1992, 66:6922-6930.
Rutledge, E. et al, J. Virol., 1998, 72:309-319.
Samulski, R., J. Virol., 1989, 63:3822-3828.
Sandalon et al, Virology, 1997, 237:414-421.
Smith, R. et al, J. Virol., 1997, 71:4461-4471.
Smith, R. et al, J. Virol., 1998, 72:4874-4881.
Smith, R. et al, J. Virol., 2000, 74:3122-3129.
Sollerbrant, K. et al, J. Gen. Virol., 2001, 82:2051-2060.
Tratschin et al, Mol. Cell Biol., 1985, 5:3251-3260.
Wu, P. et al, J. Virol., 2000, 74:8635-8647.
Xiao, W. et al, J. Virol., 1999, 73:3994-4003.
Xiao, X. et al, J. Virol., 1998, 72:2224-2232.
Xie, Q. et al, 2002, AAV-2, 99:10405-10410.
Yuan et al, Virology, 2001, 279:546-557.
Bennett and Adams, Identification of a cartilage-specific promoter within intron 2 of the chick alpha 2(I) collagen gene, J Biol Chem, 1990, p. 2223-2230, vol. 265.
Chisholm and Henner, Multiple early transcripts and splicing of the *Autographa californica* nuclear polyhedrosis virus IE-1 gene, J Virol, 1988, p. 3193-3200, vol. 62.
Reisman et al, Human p53 oncogene contains one promoter upstream of exon 1 and a second, stronger promoter within intron 1, PNAS, 1988, p. 5146-5160, vol. 85.
Kohlbrenner et al, Successful production of pseudotyped rAAV vectors using a modified baculovirus expression system, Mol Ther, 2005, p. 1217-1225, vol. 12.
Urabe et al, Scalable generation of high-titer recombinant adeno-associated virus type 5 in insect cells, J Virol, 2006, p. 1874-1885, vol. 80.
International Search Report issued in related application PCT/US07/76799 on Aug. 5, 2008.
Notification of the First Office Action issued on Sep. 27, 2010, in connection with Chinese Application No. 200780037031.2 (Chinese language).
Notification of the First Office Action issued on Sep. 27, 2010, in connection with Chinese Application No. 200780037031.2 (English translation).
International Preliminary Report on Patentability for PCT/US07/76799 mailed Feb. 24, 2009.

\* cited by examiner

EXPRESSION IN INSECT CELLS OF GENES WITH OVERLAPPING OPEN READING FRAMES, METHODS AND COMPOSITIONS THEREFOR

CROSS-REFERENCE TO RELATED APPLICATIONS

This application claims priority to U.S. Provisional Patent Application 60/839,761 filed Aug. 24, 2006, which is incorporated herein by reference in its entirety.

INTRODUCTION

Genes comprising overlapping reading frames (ORFs) are known to exist within mammalian genomes. In some cases, such genes comprise an intron which has a promoter which supports transcription of an ORF (See, e.g., Reisman, D., et al., Proc. Nat'l. Acad. Sci. USA 85: 5146-5150, 1988; Bennett, V. D., et al., J. Biol. Chem. 265: 2223-2230, 1990). However, no insect gene, either naturally occurring or artificial, has been reported which encodes multiple ORFs and comprises a promoter within an intron.

Parvoviridae comprise a family of single-stranded DNA animal viruses. The family Parvoviridae is divided between two subfamilies: the Parvovirinae, which infect vertebrates, and the Densovirinae, which infect insects. The subfamily Parvovirinae (members of which herein are referred to as the parvoviruses) includes the genus *Dependovirus*, the members of which are unique in that, under most conditions, these viruses require coinfection with a helper virus such as adenovirus or herpes virus for productive infection in cell culture. The genus *Dependovirus* includes adeno-associated virus (AAV), which normally infects humans and primates (e.g., serotypes 1, 2, 3, 3A, 3B, 4, 5, 6, 7, 8, 9, 10, & 11), and related viruses that infect other warm-blooded animals (e.g., bovine, canine, equine, and ovine adeno-associated viruses). The parvoviruses and other members of the Parvoviridae family are generally described in Kenneth I. Berns, "Parvoviridae: The Viruses and Their Replication," Chapter 69 in *FIELDS VIROLOGY* (3d Ed. 1996) and recent review article by Choi et al., Curr Gene Ther., June; 5(3):299-310 (2005).

The AAV genome is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The ITRs are self-complementary and are organized such that an energetically stable intramolecular duplex T-shaped hairpin can be formed. These hairpin structures function as an origin for viral DNA replication. The Rep genes encode the Rep proteins, Rep78, Rep68, Rep52, and Rep40. Rep78 and its splice variant Rep68 are translated from mRNAs that are transcribed from the p5 promoter. Rep52 and its splice variant Rep40 are translated from mRNAs that are transcribed from the p19 promoter. The Cap genes encode the VP proteins, VP1, VP2, and VP3. These proteins form the capsid, and are synthesized from two spliced mRNAs arising from transcription of the Cap gene from the p40 promoter. One message is translated into VP1, while another transcript encodes VP2 and VP3. The naturally occurring initiation codon for VP2 is an ACG, which is poorly utilized, resulting in ribosome scanning through to the VP3 initiation codon (AUG). The alternate usage of two splice acceptor sites for the VP1 transcript and the poor utilization of ACG initiation codon for VP2 are believed responsible for the stoichiometry of VP1, VP2, and VP3 in AAV2-infected mammalian cells and mirrors the protein ratio in the capsids, 1:1:10. Urabe, M. et al., Hum. Gene Ther. 13: 1935-1943, 2002.

An ITR of an AAV is known to function as an origin of replication, i.e., a site having a "cis" role in replication, and serves as a recognition site for trans acting replication proteins (e.g., Rep 78 or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. An AAV replicating in a mammalian cell typically has two ITR sequences.

In mammalian cells, the four Rep proteins of AAV are encoded by multiple transcripts from a single reading frame. Promoters at map positions 5 and 19 regulate transcription of the Rep ORF. Rep78 and 68 are expressed from the p5 promoter and differ from each other by a 3'-splice. Rep68 is a carboxy-truncated version of Rep78, although Rep68 contains 7 unique residues as a result of a frame shift occurring in the splice acceptor site. The Rep52 and Rep40 transcripts are expressed by the p19 promoter and are in-frame with the larger Rep polypeptides. The smaller Rep polypeptides differ from each other in the same manner as Rep78 and Rep68, i.e., by a splicing event. The functional domains of Rep are: Amino terminus-DNA binding-DNA nicking-ATPase-Helicase-nuclear localization signal-modified zinc finger-COOH. The functions of DNA binding and DNA nicking are present only in the Rep proteins transcribed from p5.

AAV replicates via a duplex DNA intermediate that is one continuous molecule: both strands are covalently attached through the ITR. The p5 Rep proteins are able to recognize a motif within the ITR, nick one strand of the duplex and become covalently attached through the tyrosinyl-thymidine phosphodiester linkage at the 5'-side of the nick. The helicase activity of Rep is believed responsible for unwinding the newly created 5'-end, and a cellular polymerase complex extends the recessed 3'-end to generate a duplex, blunt-ended replication intermediate. The smaller Rep proteins retain the ATP-dependent, DNA helicase activity and are involved in encapsidation of the single-stranded virion genomes. Rep52 and Rep40 associate with preformed capsids and, presumably, unwind the duplex replication intermediates.

In recent years, AAV has emerged as a preferred viral vector for gene therapy due to its ability to infect efficiently both nondividing and dividing cells, integrate into a single chromosomal site in the human genome, and pose relatively low pathogenic risk to humans. In view of these advantages, recombinant adeno-associated virus (rAAV) presently is being used in gene therapy clinical trials for hemophilia B, malignant melanoma, cystic fibrosis, and other diseases.

AAV sequences employed for the production of AAV in insect cells can be derived from the genome of any AAV serotype. Generally, the AAV serotypes have genomic sequences of significant sequence identity at the amino acid and the nucleic acid levels, provide a virtually identical set of genetic functions, produce virions which are essentially physically and functionally equivalent, and replicate and assemble by practically identical mechanisms. For the genomic sequence of AAV serotypes and a discussion of the genomic similarities see, for example, GenBank Accession number U89790; GenBank Accession number J01901; GenBank Accession number AF043303; GenBank Accession number AF085716; Chiorini et al., J. Vir. 71: 6823-33 (1997);

Srivastava et al., J. Vir. 45:555-64 (1983); Chiorini et al., J. Vir. 73:1309-1319 (1999); Rutledge et al., J. Vir. 72:309-319 (1998); and Wu et al., J. Vir. 74: 8635-47 (2000).

The difficulties involved in scaling-up rAAV production using current mammalian cell production systems can be significant, if not entirely prohibitive. For example, for certain clinical studies more than $10^{15}$ particles of rAAV may be required. To produce this number of rAAV particles in a mammalian cell line such as human 293 cells, transfection and culture of approximately $10^{11}$ cells, the equivalent of 5,000 175-cm$^2$ flasks of cells, would be required. There also is the possibility that a vector destined for clinical use produced in a mammalian cell culture will be contaminated with undesirable, perhaps pathogenic, material present in a mammalian cell.

U.S. Pat. No. 6,723,551 B2 to Kotin et al., and Urabe et al., J. Virol. 80: 1874-1885, 2006 disclose methods of producing rAAV vectors in insect cells. In these disclosures, baculovirus vectors were constructed that include nucleic acids that encode Rep78/68 and Rep52/40 in a palindromic head-to-tail arrangement, each of Rep78/68 and Rep 52/40 genes under the control of an independent promoter (FIG. 4 herein). These vectors include inverted terminal repeats (ITRs), transgene-encoding sequences and AAV capsid genes. While high titer rAAV was initially produced, there was no evidence that the method would be adaptable to large-scale production of rAAV. In addition, several research groups have reported that using the specific design of VP1 expression as described in U.S. Pat. No. 6,723,551 B2 produces less infectious AAV vectors as compared with their 293 cell produced counterpart. Merten et al., Gene Ther., 12: S51-S61, 2005; Kohlbrenner et al., Mol. Ther., 12: 1217-1225, 2005.

The U.S. Pat. No. 6,723,551 B2 patent also asserts that Rep mRNA splicing in insect cells does not mimic the process in mammalian cells. In particular, this reference teaches modifying a Rep68 or Rep40 coding nucleotide sequence so as to be devoid of an intron. A nucleic acid sequence to be translated in an insect cell by these methods includes only the coding sequence. Therefore, the coding sequence of any viral mRNA transcribed in this patent avoids the splicing out (removal) of an intron before translation. However, in order to express both Rep78 and Rep52 in insect cells, the methods set forth in U.S. Pat. No. 6,723,551 B2 use two separate Rep sequences and two expression cassettes, one for Rep78 and the other for Rep52.

In mammalian-cell produced AAV, the best yield of "full" virions (i.e., viral particles incorporating an AAV genome), that are fully functional and can, for example, target the nucleus, is obtained when all three VP proteins are expressed, and they are at a stoichiometry approaching 1:1:10 (VP1:VP2:VP3). The regulatory mechanisms that allow this controlled level of expression include the production of two mRNAs, one for VP1, the other for VP2 and VP3, produced by differential splicing.

The splicing event required to produce a 1:1:10 stoichiometry of VP1:VP2:VP3 is not properly reproduced in the insect cells when original AAV Cap coding sequence is used. The majority of proteins expressed from the Cap coding sequence is VP1, which is initiated from the first AUG codon of the Cap coding sequence. In order to mimic the 1:1:10 stoichiometry of VP1:VP2:VP3, the methods set forth in U.S. Pat. No. 6,723,551 B2 mutates the AUG codon of VP1 into an ACG to decrease the expression level of VP1.

Although AAV intron does not properly function in insect cells, it has been reported that the immediate-early IE-1 gene of *Autograph californica* nuclear polyhedrosis virus comprises a functional intron that can be spliced in insect cells (Chisholm and Henner, J. Virol., 62: 3193-3200, 1988). However, this reference does not suggest incorporating a promoter within the intron for expressing an operably linked open reading frame.

Various attempts have been applied to enhance the expression of VP1 of AAV, such as using chimeric VP1 protein or "riboswitch" mechanisms. See, e.g., Urabe et al., J. Virol., 80: 1874-1885, 2006 and Kohlbrenner et al., Mol. Ther., 12: 1217-1225, 2005, and U.S. patent application 2006/0166363. Furthermore, the recombinant baculovirus as described in U.S. Pat. No. 6,723,551 B2 harboring large homologous repeats of Rep78 and Rep52 has been reported unstable. Kohlbrenner et al., Mol. Ther., 12: 1217-1225, 2005. Although Kolhlbrenner et al. reported baculoviruses that are more stable and AAV vector more infectious compared to those of the U.S. Pat. No. 6,723,551 B2 patent, their techniques require separation of the coding sequences for Rep78 and Rep52 into two baculoviruses, and an additional baculovirus to supply VP1 protein.

Cao, L. et al. (J. Virology 74: 11456-11463, 2000) described a method for producing a high-titer, wild-type free recombinant adeno-associated virus vector using intron-containing helper plasmids. These methods involve insertion of a human beta-globin intron into the AAV genome. However, these methods use human cells as host, and, in addition, the introduced intron does not include a promoter that can direct transcription in insect cells.

Therefore, there remains a need for improved methods and nucleic acids for expressing genes with overlapping open reading frames in insect cells, as well as methods, nucleic acids and cells for producing infectious parvoviral vectors.

SUMMARY

In view of the need for methods of expressing genes comprising overlapping open reading frames (ORFs) in insect cells, the present inventor has developed nucleic acids, cells, cell cultures, and methods for expressing genes comprising ORFs.

In some aspects, the present teachings disclose nucleic acid cassettes. These cassettes can be used for expressing, in an insect cell, a plurality of polypeptides encoded by a gene comprising overlapping open reading frames (ORFs). A cassette of these aspects comprises, in 5' to 3' order: a) a first insect cell-operable promoter; b) a 5' portion of the gene comprising a first ORF of the gene; c) an intron comprising a second insect cell-operable promoter; and d) a 3' portion of the gene comprising at least one additional ORF of the gene, wherein the first insect cell-operable promoter is operably linked to the first ORF, the first ORF comprises a first translation initiation codon; the second insect cell-operable promoter is operably linked to the at least one additional ORF, and the at least one additional ORF comprises at least one additional translation initiation codon, and wherein at least one of a), b), c) and d) can be heterologous to at least one other of a), b), c), and d). In various configurations, a cassette can further comprise e) a polyadenylation signal situated 3' to d). In related aspects, at least one of a), b), c), d) and e) can be heterologous to at least one other of a), b), c), d) and e). In various configurations, the present teachings include vectors which comprise a nucleic acid cassette. A vector can be any type of vector known to skilled artisans, for example, a plasmid, a virus, a viral nucleic acid, or a combination thereof. In addition, in various configurations, a vector or a nucleic acid cassette can be a single- or double stranded DNA, and a virus can be a bacteriophage or a baculovirus.

In various configurations, a nucleic acid cassette of these aspects can include insect cell-operable promoters (i.e., promoters which support transcription in an insect cell). A cassette can comprise any insect cell-operable promoter known to skilled artisans. In some aspects, a first insect cell-operable promoter of a cassette can be a p10 promoter or a polh promoter and, independently, a second insect cell-operable promoter can be a p10 promoter or a polh promoter.

In various aspects of the present teachings, a gene comprising overlapping ORFs can be a gene of a virus, such as a virus that infects mammalian cells. In some aspects, the virus can be an adeno-associated virus (AAV). In some configurations, a nucleic acid cassette can comprise a first insect cell-operable promoter, a 5' portion of a Rep gene of an AAV or a 5' portion of a Cap gene of an AAV, and an intron comprising a second insect cell-operable promoter. In some arrangements, a nucleic acid comprising a Rep gene can include a Rep 78/68 ORF as a first Rep ORF and a Rep 52/40 ORF as a second or additional ORF, as described infra. Furthermore, in some configurations, the first promoter can be a p10 promoter and a second promoter can be a polh promoter. In other configurations, a nucleic acid cassette can include a Cap gene in which a first ORF can be a VP1 ORF and a second or additional ORF can be a VP2/VP3 ORF, as described infra. In some configurations, both the first and the second promoters of a nucleic acid cassette can be a polh promoter.

In yet other configurations, a single nucleic acid can comprise two or more cassettes, each cassette comprising a different gene comprising multiple ORFs. A nucleic acid can comprise cassettes arranged in a tandem, i.e., with the same polarity, or in an anti-sense orientation. Hence, a single nucleic acid in some configurations can comprise a first insect cell-operable promoter, a 5' portion of a Rep gene of an AAV, a first intron comprising a second promoter, a 3' portion of the Rep gene, a third insect cell-operable promoter, a 5' portion of a Cap gene, a second intron comprising a fourth insect cell-operable promoter, and a 3' portion of a Cap gene. In addition, in some aspects, a polyadenylation signal can be positioned 3' to each 3' portion.

The present teachings also include an insect cell comprising one or more nucleic acid cassettes which can be used to express in an insect cell a plurality of polypeptides encoded by a gene comprising multiple ORFs. An insect cell of these teachings can be an insect cell in vitro, such as an insect cell from a cultured cell line such as a BTI-Tn-5B1-4 from *Trichoplusia ni* (High-five™, Invitrogen, Carlsbad Calif.), Sf9 or Sf21, both derived from *Spodoptera frugiperda*. In various aspects, an insect cell in vitro can comprise a Rep gene of an AAV and/or a Cap gene of an AAV. Hence, in some configurations, an insect cell can comprise a first nucleic acid cassette and a second nucleic acid cassette, wherein the first nucleic acid cassette comprises a Rep 78/68 ORF and a Rep 52/40 ORF and the second nucleic acid cassette comprises a VP1 ORF and a VP2/VP3 ORF. These cassettes can each comprise a first insect-operable promoter and an intron comprising second insect-operable promoter as described herein. Cassettes in some aspects can be comprised within a cell by different nucleic acids. In other aspects, cassettes can be comprised by the same nucleic acid, in tandem or anti-sense configurations.

In some configurations, an insect cell can further include an additional nucleic acid comprising a transgene of interest to be expressed by the host insect cell. Such a nucleic acid can comprise, in some aspects, an additional cassette comprising, in 5' to 3' order, a first inverted terminal repeat (ITR) of an AAV, a mammalian cell-operable promoter; a transgene, a polyadenylation signal, and a second ITR of an AAV. A transgene of these configurations can comprise an ORF encoding any polypeptide of interest. In some configurations, a transgene can be a reporter gene, such as a chloramphenicol acetyl transferase, a β-galactosidase, a β-glucoronidase, a renilla luciferase, a firefly luciferase, a green fluorescent protein (GFP), a red fluorescent protein (RFP) or an alkaline phosphatase such as a secreted alkaline phosphatase. In other configurations, a transgene can comprise an ORF encoding a polypeptide of therapeutic interest, such as, without limitation, a polypeptide hormone, cytokine or growth factor (e.g., insulin or erythropoietin), an interferon, a blood clotting factor, or a vaccine.

In some configurations, a nucleic acid comprising a transgene of interest or a cassette comprising a gene having multiple ORFs such as a Rep gene and/or a Cap gene of an AAV can be integrated into the genome of a host insect cell. In some configurations, the integration can be a stable integration. Nucleic acids of the present teachings can also be harbored transiently in a host cell.

Some aspects of the present teachings include cell cultures. A cell culture of these aspects comprises a plurality of insect cells comprising a nucleic acid cassette comprising a first insect cell-operable promoter, a gene having overlapping open reading frames and encodes a plurality of polypeptides, and an intron comprising a second insect cell-operable promoter, as described supra; and a culture medium. In some configurations, a cell culture can comprise nucleic acid cassettes which comprise Rep and Cap genes of an AAV. In some arrangements, such cultures can produce AAV, and a culture medium of these cultures can have a titer of at least about $10^{13}$ AAV genomes/liter, at least about $10^{14}$ AAV genomes/liter, or greater. Insect cells of these configurations can be any insect cell known to skilled artisans, such as cells from cell lines BTI-Tn-5B1-4, Sf9 or Sf21. Cells of such culture can further comprise a nucleic acid comprising ITRs and a transgene, as described supra.

The present teachings also include methods of expressing a plurality of polypeptides encoded by a gene comprising overlapping ORFs. These methods can comprise, in various configurations, infecting, transforming or transfecting at least one insect cell with a nucleic acid cassette comprising a gene comprising overlapping ORFs as described herein, and culturing the at least one insect cell. Insect cells of these configurations can be any insect cell known to skilled artisans, such as cells from cell lines BTI-Tn-5B1-4, Sf9 or Sf21.

The present teachings also include methods of expressing multiple genes in an insect cell, wherein each gene comprises overlapping ORFs. These methods comprise providing one or more insect cells harboring both a first nucleic acid cassette comprising a first gene, a first insect-operable promoter and an intron comprising a second insect-operable promoter as described herein, and a second nucleic acid cassette comprising a second gene, a third insect-operable promoter and a second intron comprising a fourth insect-operable promoter. In various aspects, the cassettes of these methods can be comprised by the same or different nucleic acids, and the host insect cells can be transiently or stably transformed with either or both cassettes.

Similarly, the present teachings also include methods of producing an adeno-associated virus (AAV) in an insect cell. These methods can comprise providing one or more insect cells harboring both a first nucleic acid cassette comprising a Rep gene, a first insect-operable promoter and an intron comprising a second insect-operable promoter as described herein, and a second nucleic acid cassette comprising a Cap gene, which has a third insect-operable promoter and an intron comprising a fourth insect-operable promoter as described herein. These methods further comprise culturing the insect cells in a culture medium. In some configurations, insect cells of these methods can further comprise an additional nucleic acid, wherein the additional nucleic acid comprises a first inverted terminal repeat (ITR) of an AAV; a mammalian cell-operable promoter; a transgene, and a second ITR of an AAV. In various configurations, one or more of the cassettes and the additional nucleic acid can be comprised by one or more vectors.

In some aspects, the present teachings also include methods of producing AAV capsids in insect cells in vitro. These methods comprise: providing one or more insect cells comprising a nucleic acid cassette comprising, in 5' to 3' order, a first promoter, a 5' portion of a Cap gene of an AAV, an intron comprising a second promoter, and a 3' portion of the Cap gene; and culturing the one or more insect cells in a culture medium. In various configurations, the nucleic acid can be comprised by a vector. In some configurations, providing insect cells can comprise transforming, transfecting or infecting one or more insect cells with a nucleic acid or vector comprising the cassette. In addition, in some aspects, these methods can further comprise transforming, transfecting or infecting the cells with an additional nucleic acid which comprises a first inverted terminal repeat (ITR) of an AAV; a mammalian cell-operable promoter; a transgene, and a second ITR of an AAV.

DETAILED DESCRIPTION

Figure 1:
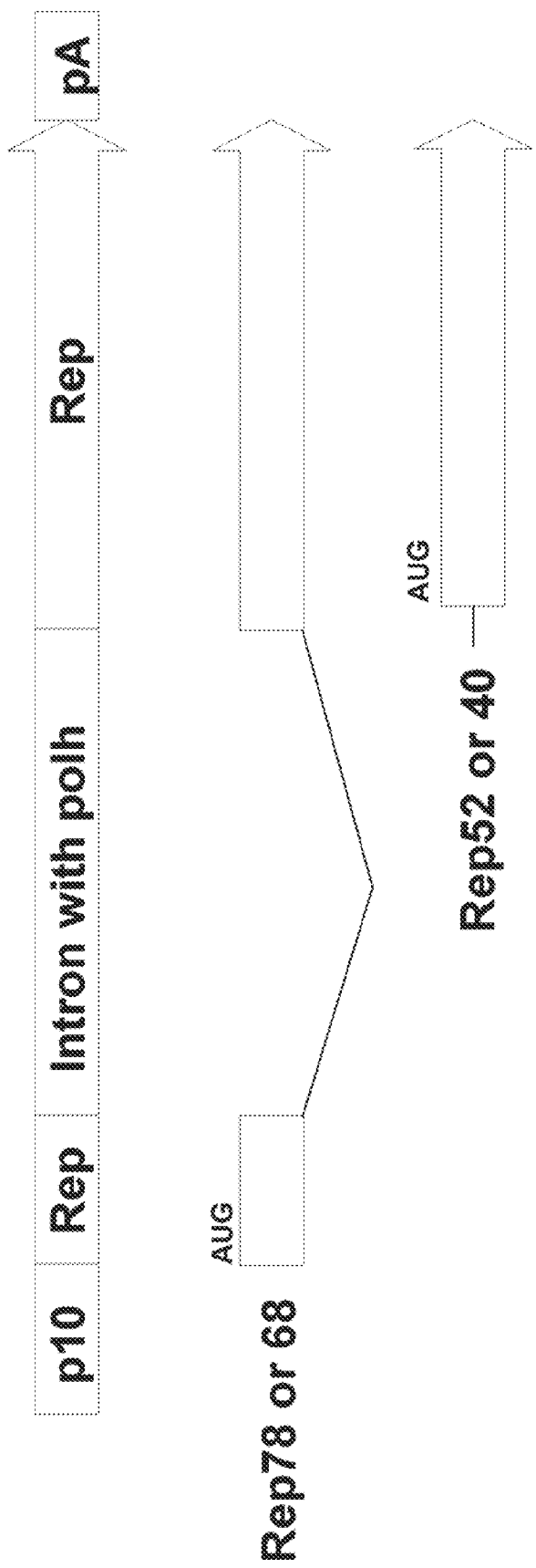
FIG. 1 illustrates a genetic and transcriptional map of representative recombinant baculovirus expressing both Rep78 or 68 and Rep52 or 40 within a single expression cassette. Mature Rep78 or 68 mRNA is formed when the artificial intron is removed through splicing. Rep52 or 40 mRNA is transcribed from the promoter located inside the artificial intron.

The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Methods In Molecular Biology, ed. Richard, Humana Press, NJ, 1995; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999. Additional references describing methods of expression of heterologous polypeptides in insect cells, as well as methods of introducing vectors and nucleic acids into insect cells and methods of maintaining insect cell cultures include, for example, O'Reilly et al., Baculovirus Expression Vectors, A Laboratory Manual, Oxford Univ. Press, 1994; Samulski et al., J. Vir. 63: 3822-3288, 1989; Kajigaya et al., Proc. Nat'l. Acad. Sci. USA 88: 4646-4650, 1991; Ruffing et al., J. Vir. 66: 6922-6930, 1992; Kimbauer et al., Vir. 219: 37-44, 1996; Zhao et al., Vir. 272: 382-393, 2000; and Samulski et al., U.S. Pat. No. 6,204,059.

As used in the description and the appended claims, the singular forms "a", "an" and "the" are intended to include the plural forms as well, unless the context indicates otherwise. All publications, patent applications, patents, and other references mentioned herein are incorporated by reference in their entirety.

The present inventor has developed a method for expressing a gene with overlapping reading frames in insect cells. The inventor has discovered that incorporating into a single gene an artificial intron comprising an insect cell-operable promoter can provide expression of overlapping open reading frames in an insect cell. "Overlapping reading frames" as used herein, refers to coding sequence from a gene which can be transcribed into multiple mRNA molecules from multiple transcription start sites; in various aspects, these mRNA molecules can be translated into multiple polypeptides. Overlapping reading frames include coding sequences which can be transcribed into mRNA molecules having different translation start sites (start codons) from one gene, with either frame-shifted reading frames or non-frame-shifted reading frames.

In some aspects, a cassette of the present teachings can comprise a Rep gene, a p10 promoter and an intron comprising a polh promoter. In various aspects, upon infection of an insect cell by a baculovirus including such a cassette, Rep78 or Rep68 pre-mRNA can be transcribed from the p10 promoter, and mature mRNA can be formed by splicing out the artificial intron. In addition, the Rep52 or Rep40 mRNA can be transcribed from a polh promoter located inside the artificial intron. As a result, an insect cell can express both Rep78 (or Rep68) and Rep52 (or Rep40) from the same Rep coding sequence, while avoiding the use of separate Rep78 and Rep52 sequences. In other aspects, any insect cell-operable promoter can be used instead of a p10 or polh promoter.

Figure 2:
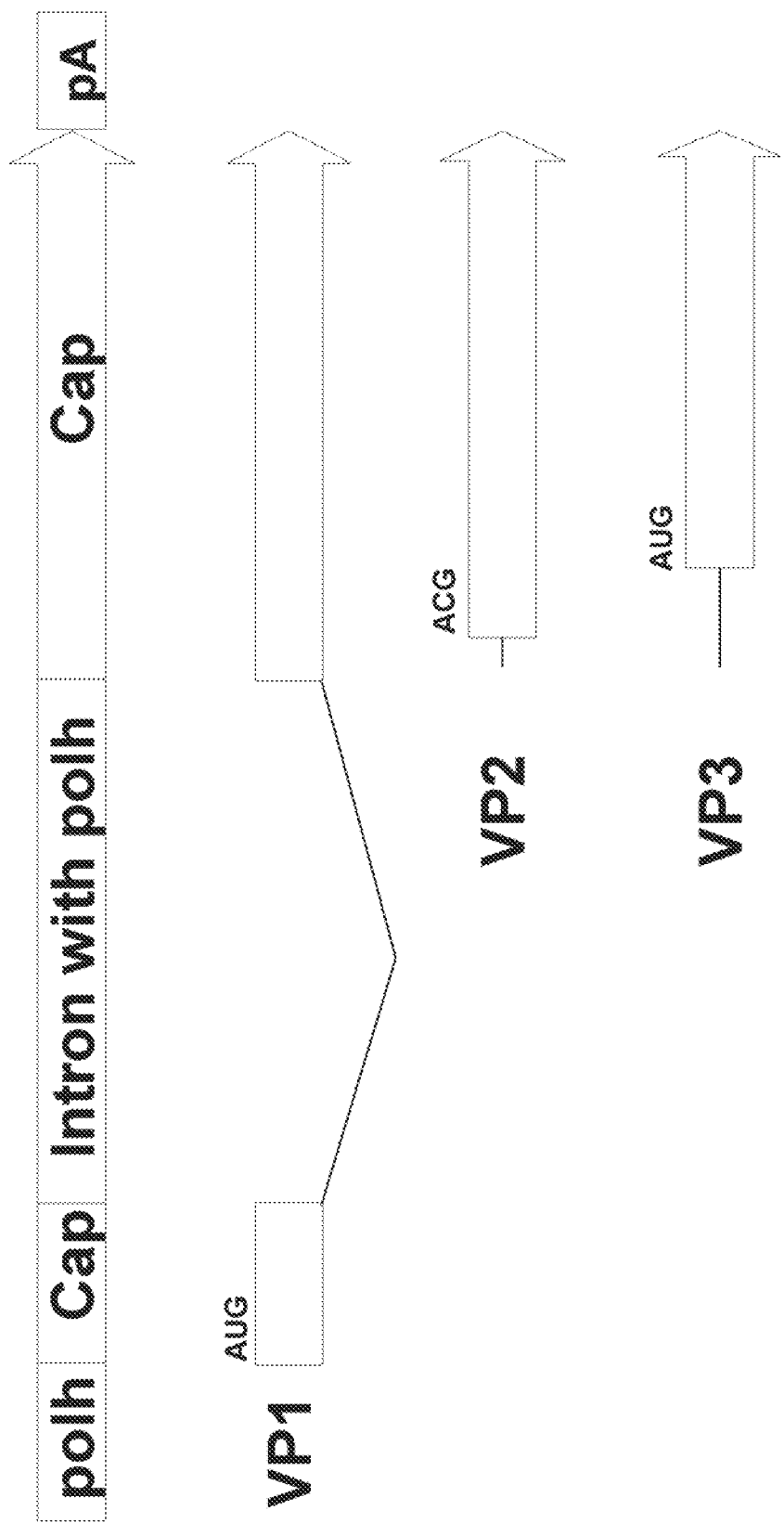
FIG. 2 illustrates a genetic and transcriptional map of representative recombinant baculovirus expressing VP1, VP2, and VP3 within a single expression cassette. Mature VP1 mRNA is formed when the artificial intron is removed through splicing. RNA encoding VP2 and VP3 is transcribed from the promoter located inside the artificial intron.

In some embodiments, the present teachings relate to the expression of overlapping Rep and Cap genes of adeno-associated virus in insect cells by incorporating into the Rep and Cap genes respectively an artificial intron comprising an insect cell-operable promoter. In some aspects, rAAV can be produced in the insect cells by employing the Rep and Cap coding sequences. By insertion of the artificial intron into the Rep coding sequence, both the Rep78 (or Rep68) and Rep52 (or Rep40) can be expressed from the single Rep coding sequence without the need to use two separate Rep coding sequences (FIG. 1). Likewise, by incorporating the artificial intron sequence into the Cap coding sequence, all three Cap proteins, VP1, VP2, and VP3, can be expressed from a single Cap coding sequence (FIG. 2). In some configurations, a Cap gene comprising an artificial intron obviates the need to mutate the VP1 initiation codon AUG into ACG as described by U.S. Pat. No. 6,723,551 B2.

In some aspects, the present teachings provides a method of producing an AAV in an insect cell. These methods comprise expressing Rep proteins and Cap proteins by transcribing mRNAs encoding the Rep proteins and Cap proteins. In these methods, at least one vector is introduced into an insect cell. A vector of these aspects comprises one or more nucleic acid molecules comprising a cassette, each cassette comprising, in 5' to 3' order, a first insect cell-operable promoter, a 5' portion of a gene comprising a first ORF of the gene comprising multiple ORFs, an intron comprising a second insect cell-operable promoter, and a 3' portion of the gene comprising at least one additional ORF. In various configurations, an insect cell-compatible vector can comprise a first nucleotide sequence comprising the Rep coding sequence and at least one artificial intron comprising an insect cell-operable promoter, and a second nucleotide sequence comprising the Cap coding sequence and at least one artificial intron. An insect cell into which such vectors are introduced can then be maintained under conditions such that AAV is produced. In some configurations, the insect cell can further comprise a nucleic acid comprising at least one AAV ITR. This nucleotide acid can also include a transgene, such as a gene encoding a reporter polypeptide or a polypeptide of therapeutic interest. In various configurations, this nucleic acid can be introduced into the cell by a vector. This vector can be distinct from the vector(s) comprising the Rep and/or Cap genes, or, in some configurations, a single vector can comprise the nucleic acid comprising at least one AAV ITR, the Rep gene and the Cap gene.

The inventor has determined that AAV Rep and ITR sequences also efficiently cross-complement other AAV Rep and ITR sequences in insect cells. Generally, the Cap proteins, which determine the cellular tropicity of the AAV particle, and related Cap protein-encoding sequences are significantly less conserved than Rep proteins and genes among different AAV serotypes. In view of the ability Rep and ITR sequences to cross-complement corresponding sequences of other serotypes, pseudotyped AAV particles comprising the capsid proteins of a serotype (e.g., AAV6) and the Rep and/or ITR sequences of another AAV serotype (e.g., AAV2) can readily be generated. As used herein, "pseudotype" refers to the source of Cap protein in an adeno-associated virus. See, e.g., Halbert, C. L., et al., J. Virol. 74: 1524-1532, 2000; Halbert, C. L., et al., J. Virol. 75: 6615-6624, 2001. For example, the inventor has produced high titers of rAAV2/6 and rAAV2/8 (i.e., pseudotyped AAV comprising the ITRs and Rep sequences of AAV2 and VP sequences derived from AAV6 and AAV8, respectively) in Sf9 cells (see Example 4). In view of the conserved nature of Rep and ITR sequences among AAV serotypes, production of a pseudotyped vector comprising the Cap genes of a particular AAV serotype in a packaging cell system indicates that nonpseudotyped vectors of that serotype also can be successfully produced in that system. For example, the efficient production of rAAV2/6 and rAAV2/8 in Sf9 cells indicates that rAAV6 and rAAV8 also can be efficiently produced in these cells.

In view of the foregoing, it will be understood that sequences from more than one AAV serotype can be combined for production of AAV in insect cells. For example, a nucleic acid comprising at least one AAV ITR nucleotide sequence can be derived from one serotype, such as AAV2, while other nucleic acids can comprise open reading frames or coding sequences derived from one or more other serotypes, such as, for example, serotype 3. In various configurations, nucleic acids of any of AAV serotypes 1, 2, 3, 4, 5, 6, 7, 8, 9, 10, and 11 can provide a Rep gene, a Cap gene, and/or an AAV ITR in the present methods.

In some aspects of these methods, an AAV ITR can be an AAV1, AAV2, or an AAV6 ITR; a nucleic acid comprising the Rep ORFs can comprise an AAV1, an AAV2, or an AAV6 Rep gene; and a nucleic acid comprising the Cap ORFs can comprise an AAV1, an AAV2, or an AAV6 Cap gene.

In some aspects, modified AAV sequences also can be used to produce rAAV in insect cells. For example, nucleotide sequences having at least about 70%, at least about 75%, at least about 80%, at least about 85%, at least about 90%, at least about 95% sequence identity to an AAV1, AAV2, AAV3, and/or AAV4 ITR, Rep, or Cap can be used in place of wild-type AAV ITR, Rep, or Cap sequences, provided that rAAV particles are produced in infected cells. Similarly, amino acid sequences having at least about 70%, at least about 75%, at least about 80%, at least about 85%, at least about 90%, at least about 95% sequence identity to an AAV1, AAV2, AAV3, and/or AAV4 polypeptide sequences can be used in place of wild-type AAV ITR, Rep, or Cap sequences, provided that rAAV particles are produced in infected cells.

In various aspects, any insect cell known to a skilled artisan which can be maintained in culture can be used with the present methods. Non-limiting examples of cell lines include Sf9 cells from *Spodoptera frugiperda*, Sf21 cells from *Spodoptera frugiperda*, *Drosophila* cell lines, or mosquito cell lines, e.g., cell lines derived from *Aedes albopictus*. In some aspects, a cell line can be a *Spodoptera frugiperda* Sf9 cell line.

Any vector known to a skilled artisan can be employed with the present teachings provided it is insect cell-compatible. The presence of a vector in the insect cell need not be permanent. The vectors can be introduced by any method known, for example by chemical treatment of the cells, electroporation, or infection. In some aspects, a vector can be a baculovirus, a viral vector, or a plasmid.

Figure 3:
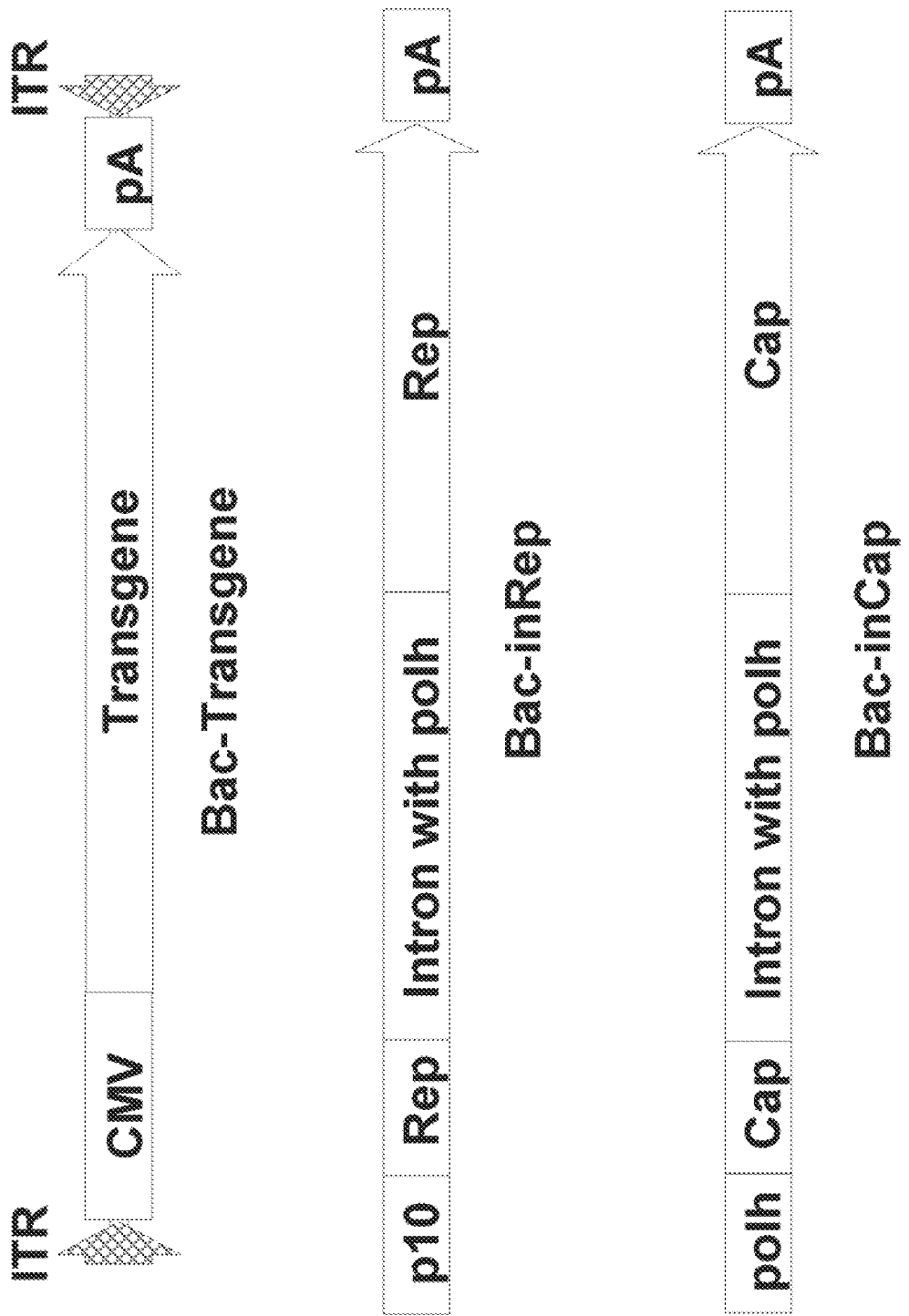
FIG. 3 illustrates a genetic map of a three-vector system for parvoviral vector production in insect cells.

If three vectors are used, a first vector can comprise a first nucleotide sequence comprising a first insect cell-operable promoter, a Rep coding sequence and an artificial intron comprising a second insect cell-operable promoter; a second vector can comprise a second nucleotide sequence comprising a third insect cell-operable promoter, Cap coding sequence and an artificial intron comprising a fourth insect cell-operable promoter; and a third nucleotide sequence comprising at least one AAV ITR nucleotide sequence. In FIG. 3, pA is a polyadenylation signal, polh and p10 are transcriptional promoters for expression in insect cells, and CMV is a mammalian transcriptional promoter for expression of a gene in a mammalian cell. ITR is an inverted terminal repeat of AAV.

Figure 4:
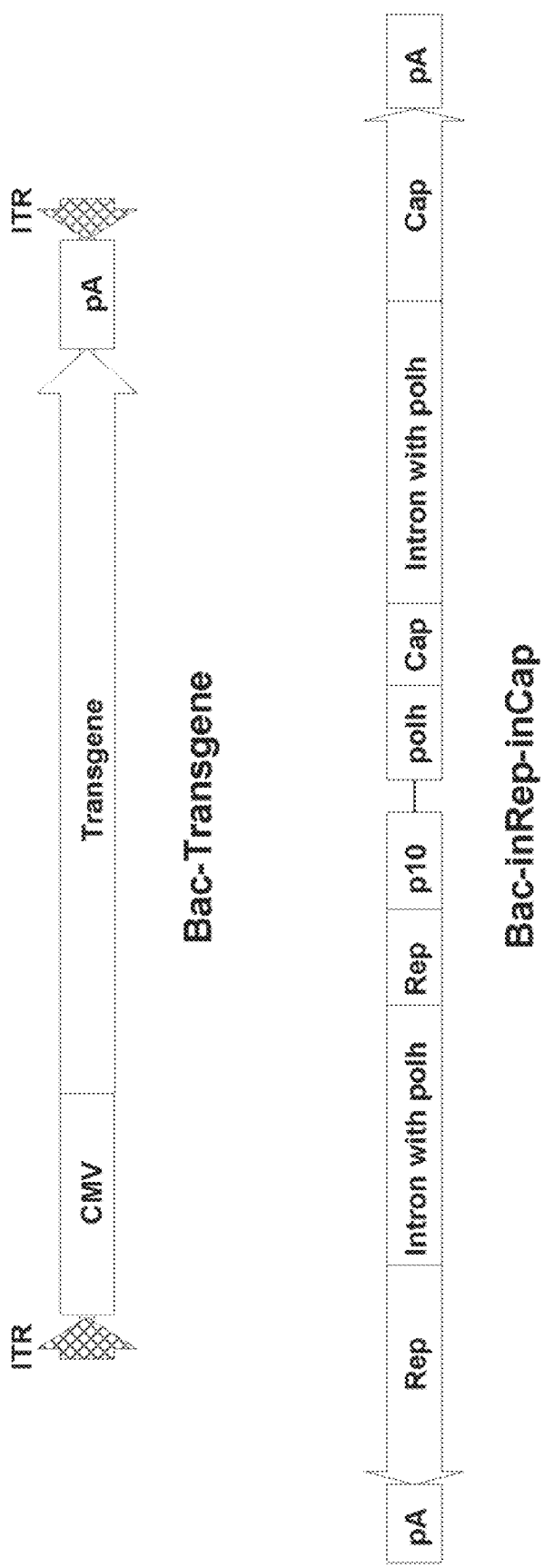
FIG. 4 illustrates a genetic map of a two-vector system for parvoviral vector production in insect cells.

In some aspects, AAV can be produced using two vectors in accordance with the disclosed methods. In these aspects, a first vector can comprise a nucleotide sequence comprising a first insect cell-operable promoter which is operably linked to a 5' portion of a Rep coding sequence, an artificial intron comprising a second insect cell-operable promoter which is operably linked to a 3' portion of the Rep coding sequence; a third insect cell-operable promoter operably linked to a 5' portion of a Cap coding sequence, and an artificial intron comprising a fourth insect cell-operable promoter which is operably linked to a 3' portion of the Cap coding sequence. A second vector of these aspects can comprise a nucleotide sequence comprising at least one AAV ITR nucleotide sequence. FIG. 4 is a genetic map of an exemplary two-vector system. In FIG. 4, pA is a polyadenylation signal, polh and p10 are transcriptional promoters for expression in insect cells, and CMV is mammalian transcriptional promoter for expression of a gene in a mammalian cell. ITR is the inverted terminal repeat of AAV.

In various configurations, the sequences comprised by each vector can be in any order relative to each other. For example, in some arrangements, a vector can comprise ITRs and a Cap coding sequence, and the Cap coding sequence can be located on the vector such that, upon replication of the DNA between ITR sequences, the Cap coding sequence can be replicated, while in other arrangements, the Cap coding sequences are not replicated. In other configurations, Rep coding sequence and the Cap coding sequence can be in any order on a vector.

Methods of introduction of nucleic acid sequences into an insect genome are well known to skilled artisans, as are methods for selecting and identifying cells harboring introduced nucleic acids. The incorporation into the genome can be aided for example, the use of a vector comprising nucleotide sequences with extensive sequence similarity to one or more regions of a genome of an insect host cell. The use of genetic elements, such as transposons, provide a method for introducing a nucleotide sequence into a genome. In some aspects of the present methods, a transformed cell can be selected or identified with the aid of a marker gene which can be encoded by a nucleic acid sequence added to the cell. The some aspects, incorporation of the nucleic acid sequence into a host cell genome then can be determined by standard methods well known to skilled artisans such as Southern blots or polymerase chain reaction (PCR) assays.

In some aspects, an ITR can be engineered so that binding sites for replication polypeptides are situated on both strands of the A regions and D regions, and are located symmetrically, one on each side of the palindrome. On a double-stranded circular DNA template (e.g., a plasmid), the Rep78- or Rep68-assisted nucleic acid replication can then proceed in both directions and a single ITR suffices for AAV replication of a circular vector. Thus, one ITR nucleotide sequence can be used in the context of the present teachings. However, two or another even number of regular ITRs can be used. In some aspects, two ITR sequences are used.

In various aspects, a nucleic acid comprising at least one AAV ITR can further comprise a nucleic acid sequence encoding at least one "gene product of interest" or "transgene" for expression in a mammalian cell, located such that it will be incorporated into an AAV genome replicated in the insect cell. Any nucleic acid can be incorporated for later expression in a mammalian cell transfected with the AAV produced in accordance with the present teachings. For example, the nucleic acid can encode a protein, express antisense RNA, or small interfering RNA (SiRNA). The protein can be a secretory protein, or a protein which will affect primarily the cell that is infected with the insect-produced AAV. In some aspects, a product of interest can be Rep78 or Rep68. Accordingly, in these aspects, a nucleotide sequence can comprise two nucleic acid sequences, each encoding one gene product of interest for expression in a mammalian cell. Each of the two nucleic acid sequences encoding a product of interest can be arranged such that it will be incorporated into an rAAV genome replicated in an insect cell.

In various configurations, a product of interest can be a gene product which can be a polypeptide or an RNA molecule. Non-limiting examples of a polypeptide of interest include proteins such as an enzyme, a clotting factor, a peptide hormone or a fusion protein. Other examples of products of interest include a gene product which complements a genetic defect, an RNA molecule, or a transcription factor. For example, a gene product of interest can comprise a nucleotide sequence that provides a regulatory function (e.g., a transposon). Examples of gene products of interest include, but are not limited to: hormone receptors (e.g., mineralcorticosteroid, glucocorticoid, and thyroid hormone receptors); intramembrane proteins (e.g., TM-1 and TM-7); intracellular receptors (e.g., orphans, retinoids, vitamin D3 and vitamin A receptors); signaling molecules (e.g., kinases, transcription factors, and signal transducers and activators of transcription receptors of the cytokine superfamily (e.g. erythropoietin, growth hormone, interferons, and interleukins, and colony-stimulating factors; G-protein coupled receptors, e.g., hormones, calcitonin, epinephrine, gastrin, and paracrine or autocrine mediators, such as stomatostatin or prostaglandins; neurotransmitter receptors (norepinephrine, dopamine, serotonin or acetylcholine); pathogenic antigens, which can be of viral, bacterial, allergenic, or cancerous origin; and ligands of tyrosine kinase receptors (such as insulin growth factor, and nerve growth factor).

In various aspects, a gene product of interest can be a therapeutic gene product. A therapeutic gene product can be a polypeptide, RNA molecule, or other gene product that, when expressed in a target cell, provides a therapeutic effect, such as, for example, ablation of an infected cell (e.g., as described by Goldsmith et al., WO 90/07936), expression of a polypeptide having a therapeutic biological activity, and/or expression of an RNA molecule for antisense therapy (e.g., regulation of expression of a endogenous or heterologous gene in a target cell genome). For example, in a patient about to receive a heterologous transplant or graft, one may administer a polynucleotide encoding a toxin to T cells targeting the graft.

An AAV protein can be a gene product of interest. For example, the sequence of a Rep protein, such as Rep78 or Rep68, or a functional fragment thereof can be a gene product of interest for expression in a mammalian cell. A nucleic acid sequence encoding Rep78 and/or Rep68, if present in a rAAV genome of the present teachings and expressed in a mammalian cell transduced with the rAAV produced in accordance with the present teachings, allows for integration of the rAAV into the genome of the transduced mammalian cell. Expression of Rep78 and/or Rep68 in an rAAV-transduced or infected mammalian cell can bestow an advantage for certain uses of the rAAV produced in an insect cell, such as allowing long term or permanent expression of any other gene product of interest introduced in the cell by the rAAV.

A selectable marker is one type of a gene product of interest. Expression of a protein encoded by the selectable marker allows a host cell transfected with an expression vector which includes the selectable marker to be distinguished from a host cell which does not have the expression vector encoding the selectable marker. An example is a host cell which can use the selectable marker to survive a selection process that would otherwise kill the host cell, such as treatment with an antibiotic. Such a selectable marker can be one or more antibiotic resistance factors, such as neomycin resistance (e.g., neo), hygromycin resistance, and puromycin resistance. A selectable marker also can be a cell-surface marker, such as nerve growth factor receptor or truncated versions thereof. Cells that express the cell-surface marker then can be selected using an antibody targeted to the cell-surface marker. The antibody targeted to the cell surface marker can be directly labeled (e.g., with a fluorescent substrate) or can be detected using a secondary labeled antibody or substrate which binds to the antibody targeted to the cell-surface marker. Alternatively, cells can be negatively selected by using an enzyme, such as Herpes simplex virus thymidine kinase (HSVTK) that converts a pro-toxin (gancyclovir) into a toxin or bacterial Cytosine Deaminase (CD) which converts the pro-toxin 5'-fluorocytosine (5'-FC) into the toxin 5'-fluorouracil (5'-FU). Alternatively, any nucleic acid sequence encoding a polypeptide can be used as a selectable marker as long as the polypeptide is easily recognized by an antibody.

A nucleic acid encoding a selectable marker can encode, for example, a beta-lactamase, a luciferase, a green fluorescent protein (GFP), a beta-galactosidase, or other reporter gene as that term is understood in the art, including cell-surface markers, such as CD4 or the truncated nerve growth factor (NGFR) (for GFP, see WO 96/23810; Heim et al., Current Biology 2:178-182 (1996); Heim et al., Proc. Natl. Acad. Sci. USA (1995); or Heim et al., Science 373:663-664 (1995); for beta-lactamase, see WO 96/30540). In some aspects, a selectable marker can be a beta-lactamase. The nucleic acid encoding a selectable marker can encode, for example, a fluorescent protein. A fluorescent protein can be detected by determining the amount of any quantitative fluorescent property, e.g., the amount of fluorescence at a particular wavelength, or the integral of fluorescence over an emission spectrum. Techniques for measuring fluorescence are well-known to persons of skill in the art.

In various aspects, a nucleic acid for expression in the mammalian cell can be incorporated into the AAV genome produced in the insect cell if it is located between two regular ITRs, or is located on either side of an ITR engineered with two D regions.

In various aspects, a nucleotide sequence encoding a gene product of interest for expression in a mammalian cell can be operably linked to at least one mammalian cell-compatible expression control sequence, e.g., a promoter. Many such promoters are known in the art. It will be understood by a skilled artisan that promoters of these aspects include those that are inducible, tissue-specific, and/or cell cycle-specific. For example, an E2F promoter can mediate tumor-selective, and, in particular, neurological cell tumor-selective expression in vivo by being de-repressed in such cells in vivo. Parr et al., Nat. Med. 3: 1145-1149 (1997). In addition, in some configurations, more than one expression control sequence can be operably linked to a given nucleotide sequence. For example, a promoter sequence, a translation initiation sequence, and a stop codon can be operably linked to a nucleotide sequence.

Splice sites are sequences on a mRNA which facilitate the removal of parts of the mRNA sequences after the transcription (formation) of the mRNA. Typically, the splicing occurs in the nucleus, prior to mRNA transport into a cell's cytoplasm.

In some aspects, an expression control sequence can share sequence identity with known expression control sequences. A determination of the degree of sequence identity of two nucleic acids sequences is a determination of the percentage of time a nucleotide, from among the four known natural nucleotides, exactly matches a counterpart on a second nucleotide sequence, i.e., a T matches a T, an A matches an A, a G matches a G, and a C matches a C. A sequence identity of at least 50%, 60%, 70%, 80%, 90% or more, can be considered to have substantial sequence similarity with an expression control sequence. In some aspects, sequence identity can be calculated between sequences without introduction of gaps in one or both of the sequences being compared.

A skilled artisan will understand that in order to optimize the sequence similarity between two nucleotide sequences, gaps can be introduced in either or both of the two sequences. In some aspects, if gaps are introduced, only nucleotides of a first sequence which pair with a nucleotide in a second nucleotide sequence (whether or not there is a match) are used to calculate percentage homology. Algorithms that have worked out the rules of calculation of percentage homology are known. Examples of such programs include the SIM, GAP, NAP, LAP2, GAP2, ALIGN, BLAST, and PIPMAKER.

For example, the ALIGN program produces an optimal alignment of two chosen protein or nucleic acid sequences using a modification of the dynamic programming algorithm described by Myers and Miller, CABIOS, 4, 11-17 (1988). Preferably, if available, the ALIGN program is used with weighted end-gaps. If gap opening and gap extension penalties are available, they are preferably set between about −5 to −15 and 0 to −3, respectively, more preferably about −12 and −0.5 to −2, respectively, for amino acid sequence alignments, and −10 to −20 and −3 to −5, respectively, more preferably about −16 and −4, respectively, for nucleic acid sequence alignments. The ALIGN program and principles underlying it are further described in, e.g., Pearson et al., Proc. Natl. Acad. Sci. USA, 85: 2444-48 (1988), and Pearson et al., Methods Enzymol. 183:63-98 (1990).

The BLAST programs provide analysis of at least two amino acid or nucleotide sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations (see, e.g., Wooton et al., Compu. Chem., 17:149-63 (1993); Altschul et al., Nat. Genet., 6: 119-29 (1994); Hancock et al., Comput. Appl. Biosci., 10:67-70 (1994); and Wootton et al., Meth. in Enzym., 266:554-71 (1996)). If a lambda ratio is used, preferred settings for the ratio are between 0.75 and 0.95, more preferably between 0.8 and 0.9. If gap existence costs (or gap scores) are used, the gap existence cost preferably is set between about −5 and −15, more preferably about −10, and the per residue gap cost preferably is set between about 0 to −5, more preferably between 0 and −3 (e.g., −0.5). Similar gap parameters can be used with other programs as appropriate. The BLAST programs and principles underlying them are further described in, e.g., Altschul et al., J. Mol. Biol., 215: 403-10 (1990), Karlin and Altschul, Proc. Natl. Acad. Sci. USA, 87: 2264-68 (1990) (as modified by Karlin and Altschul, Proc. Natl. Acad. Sci. USA, 90: 5873-77 (1993)), and Altschul et al., Nucl. Acids Res., 25: 3389-3402 (1997).

In some aspects of the methods disclosed herein, it is possible to use less than the four Rep enzymes, such as only one of the Rep78/Rep68 enzymes and only one of the Rep52/Rep40 enzymes, wherein both of the enzymes are expressed from the same single Rep coding sequence comprising the artificial intron. Since the AAV p5 and p19 promoters function poorly in insect cells, an insect cell-operable promoter, e.g., p10 or polh promoter, replaces the p5 and p19 promoters for Rep78/68 and Rep52/40. Because the p19 promoter is located in the Rep coding region, replacing p19 promoter with any other promoter changes the codons of Rep ORF and therefore the functions of Rep78/68 protein.

Methods of the present teachings utilize an artificial intron that functions in insect cells and provides a method of inserting an insect cell-operable promoter into the p19 promoter area without changing the Rep78/68 coding sequence and functions, and makes it possible to express both Rep78 and Rep52 or Rep68 and Rep40 from a single expression cassette. In some aspects, the Rep coding sequence can comprise an artificial intron comprising the polh promoter (FIG. 1). In some configurations, the sequence of the artificial intron comprising the polh promoter can be: GTAAGTACTCCCTAT-CAGTGATAGAGATCTATCATG-GAGATAATTAAAATGA TAACCATCTCGCAAATAAATAAGTATTT-TACTGTTTTCGTAACAGTTTTGTAA TAAAAAAAC-CTATAAATATTCCGGATTATTCATAC-CGTCCCACCATCGGGCGC GAAGGGGGAGACCTGTAGTCAGAGC-CCCCGGGCAGCACACACTGACATCCA CTCCCTTC-CTATTGTTTCAG (SEQ ID NO: 1). The polh promoter within this artificial intron is ATCATGGAGATAAT-TAAAATGATAACCATCTCG-CAAATAAATAAGTATTTTA CTGTTTTCGTAA-CAGTTTTGTAATAAAAAAACCTATAAATATTCCGGATTAT CATACCGTCCCACCATCGGGCGCG (SEQ ID NO: 20). In some aspects, the artificial intron can be inserted into the Rep coding sequence between nucleotides 850 and 851 according to the AAV genome (NCBI accession no. AF043303) such that the Rep52 or Rep40 protein can be expressed from the polh promoter, while the Rep78 or Rep68 protein can be synthesized from the p10 promoter located upstream of the Rep coding sequence. In various other aspects, the artificial intron can be inserted into locations other than nucleotides 850 and 851.

In some aspects, the present teachings disclose using an artificial intron to express all three Cap proteins (VP1, VP2, and VP3) from a single Cap coding nucleotide without mutating the AUG translation initiation codon of VP1 protein. In some configurations, an artificial intron is inserted between nucleotides 2227 and 2228 according to the AAV genome (AF043303) such that the VP2 and VP3 proteins can be synthesized from a polh promoter situated within the artificial intron, whereas the VP1 protein can be expressed from a polh promoter located upstream of the Cap coding sequence (FIG. 2). Upon infection of insect cells by baculovirus carrying the Cap coding sequence comprising the artificial intron, the VP1 pre-mRNA can be transcribed from the promoter upstream of the Cap coding region and mature mRNA can be formed by splicing out the artificial intron. The mature mRNA can then be translated into VP1 protein using its original AUG instead of ACG initiation codon so that the original VP1 amino acid composition is not altered as described by U.S. Pat. No. 6,723,551 B2. In addition, the VP2 and VP3 mRNA can be transcribed from the polh promoter located inside the artificial intron. In accordance with a preferred embodiment, both of the promoters located upstream of the Cap coding sequence and inside the artificial intron are the polh promoter.

In various aspects of the present teachings, variations of the artificial intron sequence can be used in the disclosed methods. In some configurations, a sequence with substantial sequence similarity to an artificial intron nucleotide sequence can be utilized. For example, a sequence of at least 60%, 70%, or 90% sequence identity to the artificial intron nucleotide sequence of SEQ ID NO: 1 can be introduced into a cassette such that both the Rep78 (or Rep68) and Rep52 (or Rep40), or all three Cap proteins (VP1, VP2, and VP3) can be expressed.

Figure 5:
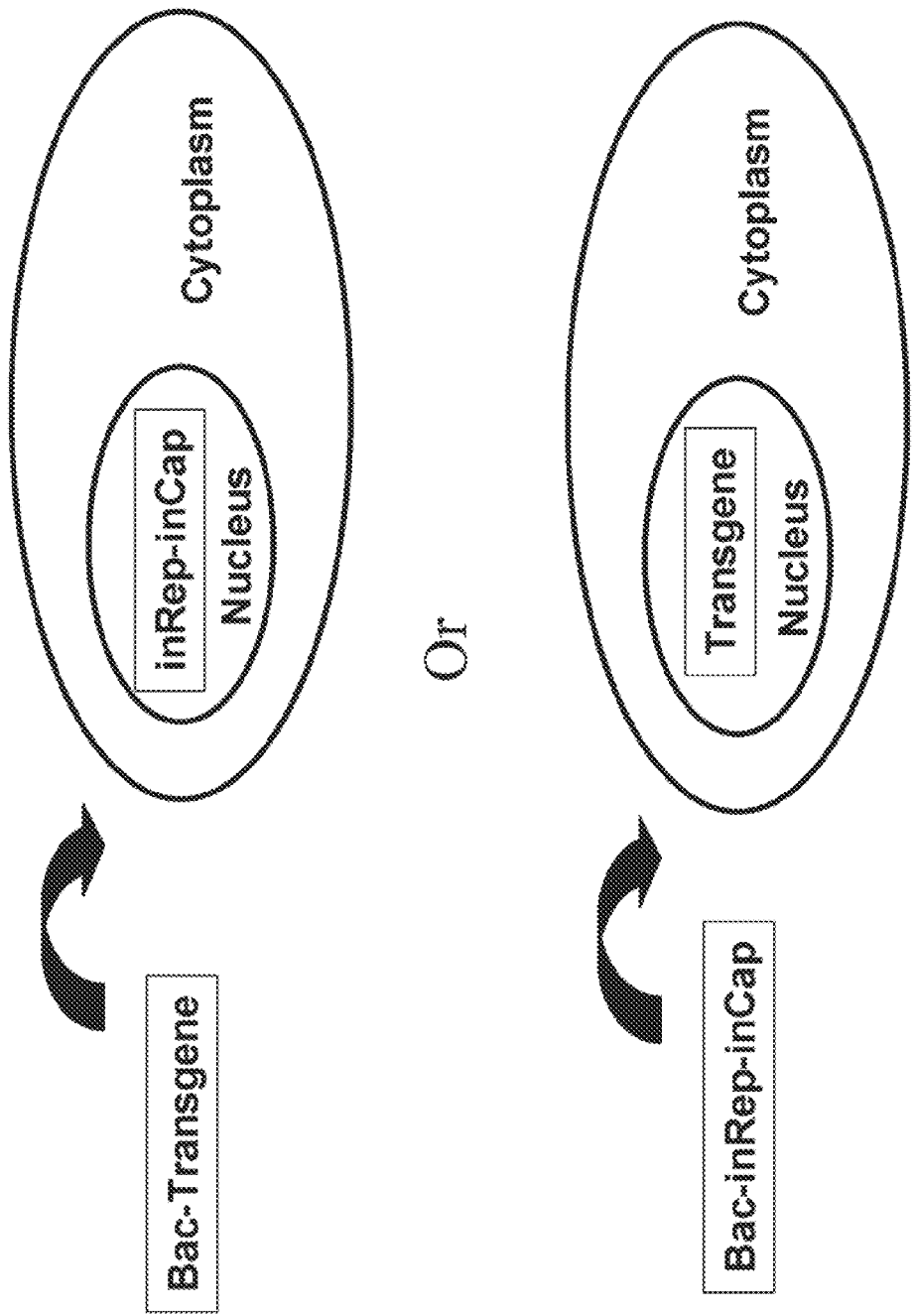
FIG. 5 illustrates two examples of a single-vector system together with a stable insect cell line for producing AAV vectors in insect cells.

In various aspects of the present teachings, an insect cell-compatible vector comprising at least one nucleotide sequences of the present teachings is provided. In some configurations, a vector can comprise an AAV Rep-encoding nucleotide sequence, and further comprise an artificial intron comprising an insect cell-operable promoter. In accordance with another configuration, an insect cell-compatible vector can comprise an AAV Cap-encoding nucleotide sequence, and further comprise an artificial intron of nucleotide sequence of SEQ ID NO: 1 or a nucleotide sequence having substantial sequence identity with the sequence set forth as SEQ ID NO: 1. In some configurations, the AAV capsid proteins VP1, VP2 and VP3 can be from AAV2. FIG. 5 provides two examples of a single vector together with a stable cell line for AAV production.

In various aspects of the present teaching, an insect cell is disclosed comprising at least one of a first nucleotide sequence, a second nucleotide sequence and a third nucleotide sequence. In these aspects, a first nucleotide sequence can comprise a first insect cell-operable promoter, a 5' portion of Rep-encoding nucleotide sequence, an artificial intron comprising a second insect cell-operable promoter, and a 3' portion of the Rep-encoding nucleotide sequence, wherein the first insect cell-operable promoter is operably linked to the 5' portion of the Rep-encoding nucleotide sequence and the second insect cell-operable promoter is operably linked to the 3' portion of the Rep-encoding nucleotide sequence. Furthermore, in these aspects, a second nucleotide sequence can comprise a third insect cell-operable promoter, a 5' portion of a Cap-encoding nucleotide sequence, an artificial intron comprising a fourth insect cell-operable promoter, and a 3' portion of the Cap-encoding nucleotide sequence, wherein the third promoter is operably linked to the 5' portion of the Cap-encoding nucleotide sequence and the fourth promoter is operably linked to the 3' portion of the Cap-encoding nucleotide sequence. In addition, an insect cell of these teachings can comprise a first nucleotide sequence comprising at least one AAV ITR nucleotide sequence.

In some aspects of the present teachings, a nucleotide sequence comprised by an insect cell can comprise two AAV ITR nucleotide sequences and at least one nucleotide sequence encoding a gene product of interest or a transgene for expression in a mammalian cell between the two AAV ITR nucleotide sequences. In various configurations, at least one of the first, second, and third nucleotide sequences can be stably integrated in the insect cell.

Figure 6:
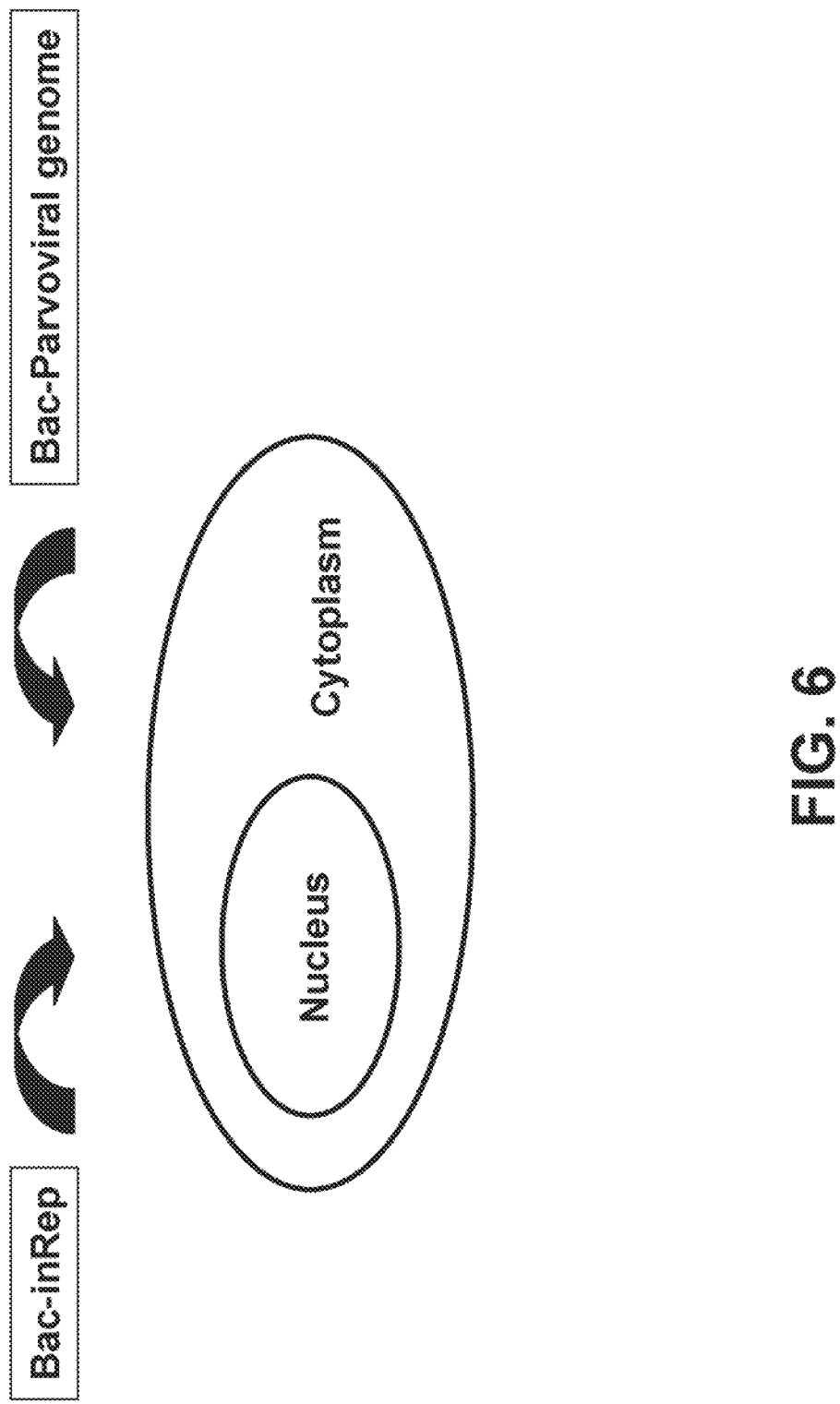
FIG. 6 illustrates an example of a method for parvoviral genome production.

In another aspect, the present teachings provide a method of producing a parvoviral genome in an insect cell. In the method, as illustrated in FIG. 6, one or two insect cell-compatible vectors can be introduced to an insect cell. These vectors can collectively comprise a first nucleotide sequence and a second nucleotide sequence. A first nucleotide sequence of these aspects can comprise a first insect cell-operable promoter, a 5' portion of a Rep coding sequence, an artificial intron-comprising a second insect cell-operable promoter, and a 3' portion of the Rep coding sequence, wherein the first promoter is operably linked to the 5' portion of the Rep coding sequence and the second promoter is operably linked to the 3' portion of the Rep coding sequence. A second nucleotide sequence of these aspects can comprise a second nucleotide sequence that includes at least one parvoviral ITR. In various configurations of the methods, after introducing the vector or vectors to an insect cell, the insect cell can be maintained under conditions such that a parvovirus genome is produced therein. The parvoviral genome can be any nucleic acid that (1) comprises 5' and 3' ITRs from or having substantial sequence identity (e.g., at least about 70% identity, at least about 80% identity, at least about 90% identity, at least about 95% identity, or greater) to AAV 5' and 3' ITRs, respectively, and (2) can replicate in the insect cell upon the introduction of one or more vectors. In some configurations, the parvoviral genome can further include Rep sequences or sequences sharing substantial identity thereof. A parvovirus of these aspects can be any member of the Parvovirinae. In particular, a parvovirus can be a parvovirus which infects mammals. In some aspects, a parvovirus can be a *dependovirus* such as an AAV, for example a human or a simian AAV. A parvovirus genome produced in an insect cell in accordance with the present teachings can include wild-type and/or modified ITRs, Rep sequences, and VP sequences, as well as one or more additional nucleotide sequences (e.g., one or more transgenes).

Figure 7:
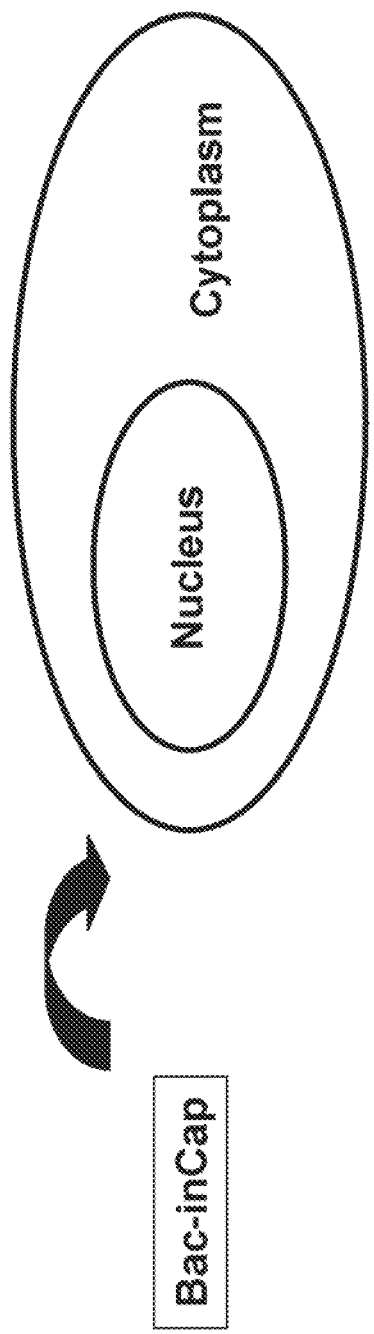
FIG. 7 illustrates an example of a method for empty parvoviral particle production.

In yet another aspect, the present teaching disclose methods of producing empty parvoviral particles in an insect cell. In these method, illustrated in FIG. 7, an insect cell-compatible vector can be introduced to an insect cell, and maintained under conditions such that an empty parvoviral particle is produced therein. The empty parvoviral particle can be any parvoviral capsids. The parvovirus can be any suitable member of the Parvovirinae, such as a parvovirus which infects mammals. In some aspects, a parvovirus can be a *dependovirus*, such as a human or simian AAV. In various configurations, an empty parvovirus particle produced in an insect cell can include wild-type and/or modified Cap sequences.

EXAMPLES

Various aspects of the present teachings can be illustrated by the following non-limiting examples. The following examples are illustrative, and are not intended to limit the scope of the claims. The description of a composition or a method in an example does not imply that a described article or composition has, or has not, been produced, or that a described method has, or has not, been performed, except for results presented in past tense.

Example 1

This example demonstrates that a single nucleic acid comprising a AAV2 Rep coding sequence and an artificial intron comprising the polh promoter can express both Rep78 and Rep52 proteins.

Figure 8:
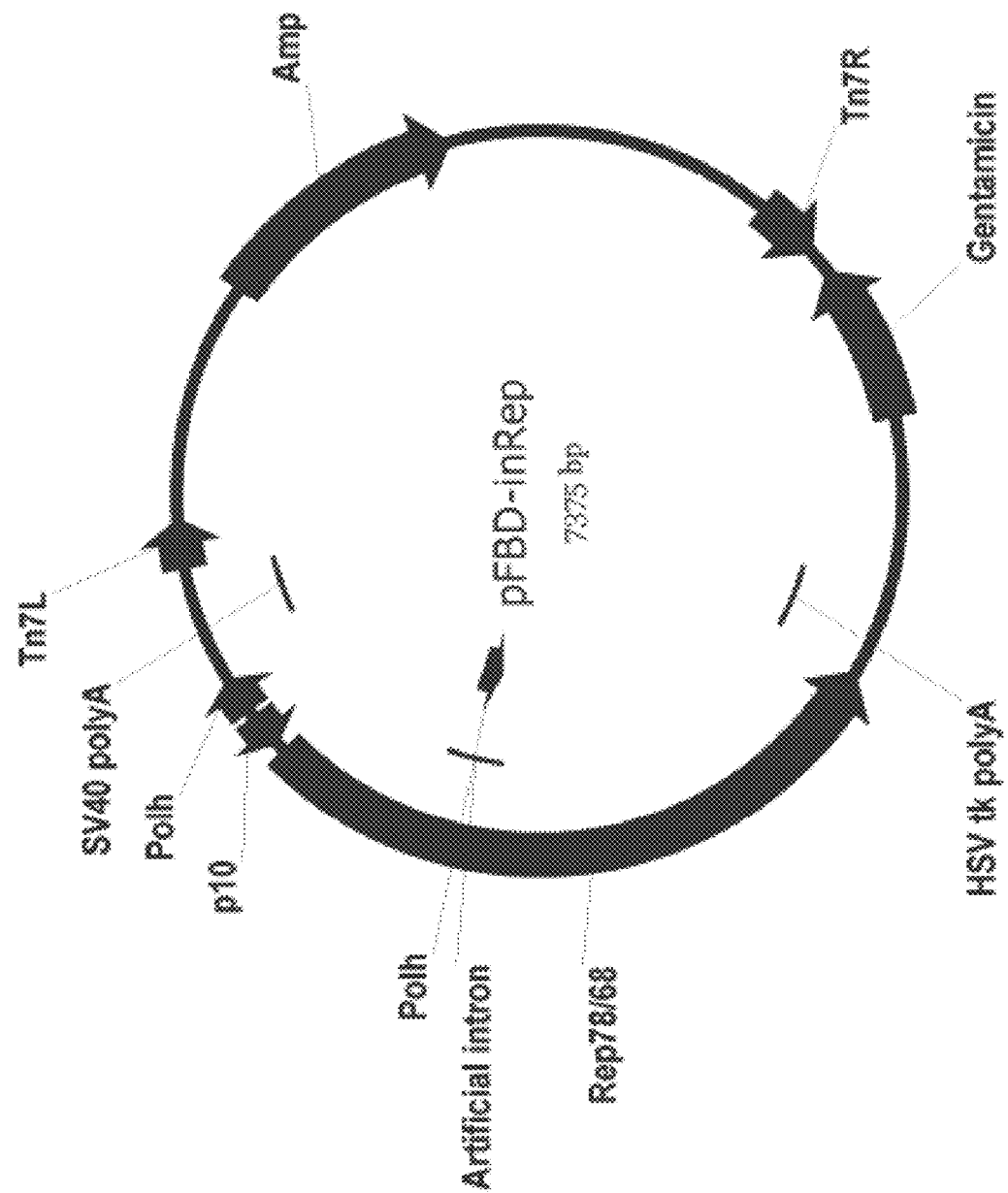
FIG. 8 illustrates a genetic map of a recombinant vector comprising AAV2 Rep coding sequence comprising an artificial intron comprising a polyhedrin (polh) promoter. This vector can be used for the production of AAV vectors in insect cells.

In these experiments, an artificial intron comprising the polh promoter was designed using similar splicing donor and acceptor sequences as reported by Chisholm and Henner J Virol. 62(9):3193-3200 (1988). An artificial intron (SEQ ID NO: 1) is inserted into the Rep78 sequence such that the Rep52 mRNA is transcribed from the polh promoter located inside the artificial intron, whereas the Rep78 pre-mRNA is transcribed from the p10 promoter located upstream from the Rep78 start codon. Upon removal by splicing of the artificial intron by the host cell, mature Rep78 mRNA is formed (FIG. 1). In these experiments, the artificial intron was inserted between nucleotides 850 and 851 according to standard numbering of the AAV genome (available on the internet at http://www.ncbi.nlm.nih.gov/entrez/viewer.fcgi?db=nuccore&id=2906016, accession no. AF043303; see also Srivastava, A., et al., J. Virol. 45: 555-564, 1983) wherein the sequence of nucleotides 841-860 is agtatttaag cgcctgtttg (SEQ ID NO: 25). The plasmid pAAV-RC (Stratagene, La Jolla, Calif.) was first digested with HindIII and SacI to isolate the backbone fragment (6259 bp). Then the pAAV-RC was digested with DrdI and HindIII to isolate a 977 bp-fragment. Finally 12 oligos comprising the artificial intron containing the polh promoter were synthesized and annealed. The 6259 bp-backbone fragment, the 977 bp-fragment, and the annealed oligos were ligated to create plasmid pAAV-inRC. The Rep coding sequence containing the artificial intron was amplified by a polymerase chain reaction (PCR) using PCR primers 5'-GTGTGTATAC-CCGCCATGCCGGGGTTTTACGAGAT-3' (SEQ ID NO:14) and 5'-GCGCGCATGCTCCTTCAGAGAGAGT-GTCCTCGAGC-3' (SEQ ID NO:15) and digested with restriction endonucleases BstZ17I and SphI, and cloned into the SmaI and SphI sites of pFastBacDual (Invitrogen, Carlsbad, Calif.) to create pFBD-inRep (FIG. 8). The 12 oligos used to form the artificial intron are as follows:

(SEQ ID NO: 2)
5'-CAGTGGGCGTGGACTAATATGGAACAGTATTTAAGGTAAGTACTCCC
TATCAGTGATAG-3'

(SEQ ID NO: 3)
5'-AGATCTATCATGGAGATAATTAAAATGATAACCATCTCGCAAATAAA
TAAGTATTTTACT-3'

(SEQ ID NO: 4)
5'-GTTTTCGTAACAGTTTTGTAATAAAAAAACCTATAAATATTCCGGAT
TATTCATACCGTC-3'

(SEQ ID NO: 5)
5'-CCACCATCGGGCGCGAAGGGGGAGACCTGTAGTCAGAGCCCCCGGGC
AGCACACACTGAC-3'

(SEQ ID NO: 6)
5'-ATCCACTCCCTTCCTATTGTTTCAGCGCCTGTTTGAATCTCACGGAG
CGTAAACGGTTGG-3'

(SEQ ID NO: 7)
5'-TGGCGCAGCATCTGACGCAC-3'

(SEQ ID NO: 8)
5'-GCGTCAGATGCTGCGCCACCAACCGTTTACGCTCCGTGAGATTCAAA
CAG-3'

(SEQ ID NO: 9)
5'-GCGCTGAAACAATAGGAAGGGAGTGGATGTCAGTGTGTGCTGCCCGG
GGGCTCTGACTAC-3'

(SEQ ID NO: 10)
5'-AGGTCTCCCCCTTCGCGCCCGATGGTGGGACGGTATGAATAATCCGG
AATATTTATAGGT-3'

(SEQ ID NO: 11)
5'-TTTTTTATTACAAAACTGTTACGAAAACAGTAAAATACTTATTTATT
TGCGAGATGGTTA-3'

(SEQ ID NO: 12)
5'-TCATTTTAATTATCTCCATGATAGATCTCTATCACTGATAGGGAGTA
CTTACCTTAAATA-3'

(SEQ ID NO: 13)
5'-CTGTTCCATATTAGTCCACGCCCACTGGAGCT-3'

The plasmid pFBD-inRep was used to transform DH10Bac competent cells and recombinant Bacmid DNA containing the Rep coding sequence was isolated and used to generate recombinant baculovirus Bac-inRep in Sf9 cells according to the manufacturer's protocol (Invitrogen, Carlsbad, Calif.). Sf9 cells were maintained at 28° C. in SF900 II SFM containing 100 units/ml of penicillin and 100 µg/ml of streptomycin (Invitrogen, Carlsbad, Calif.).

Figure 9:
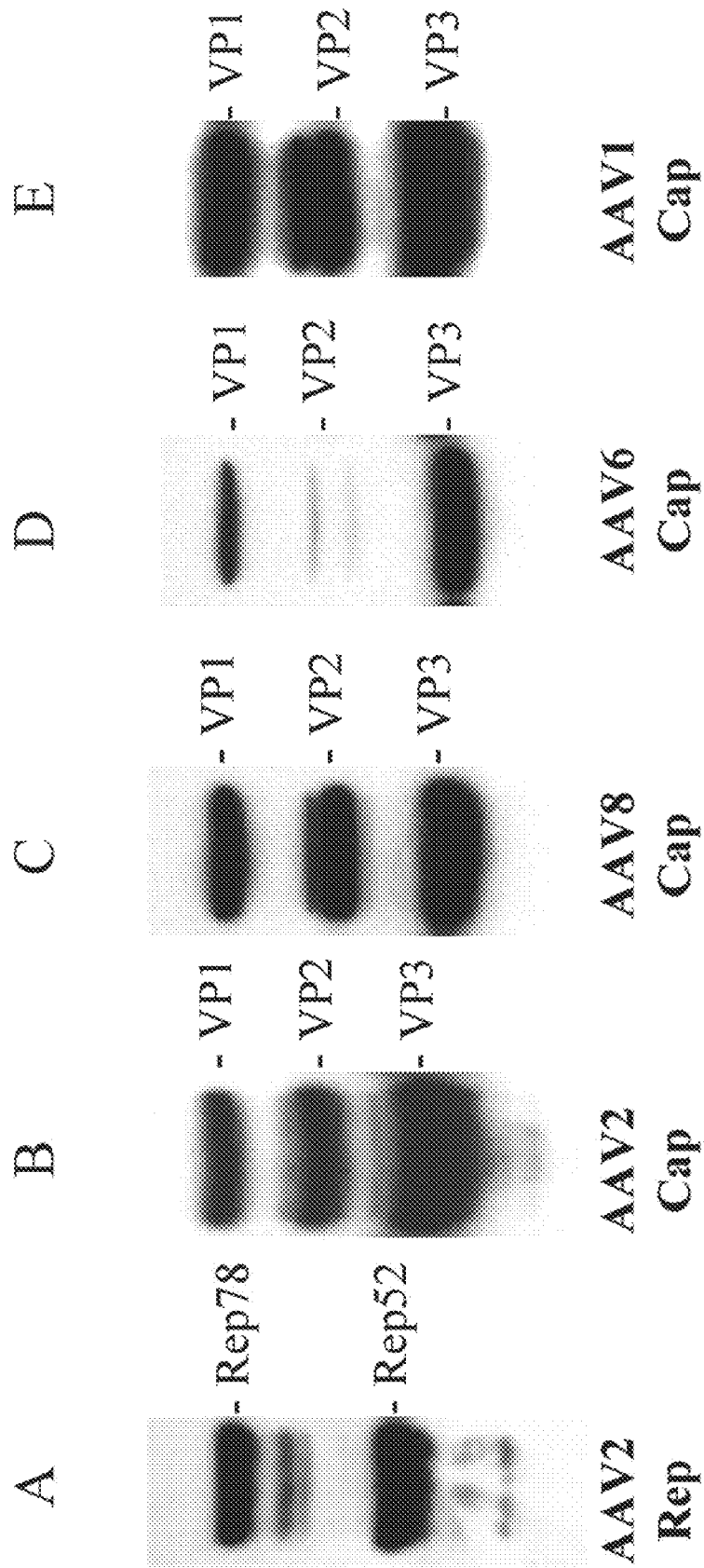
FIG. 9 illustrates representative results of Western blots of Rep and Cap proteins. (A) AAV2 Rep78 and Rep52 expressed from Sf9 cells infected with Bac-inRep; (B) AAV2 Cap proteins expressed from Sf9 cells infected with Bac-inCap; (C) AAV8 Cap proteins expressed from Sf9 cells infected with Bac-inCap8; (D) AAV6 Cap proteins expressed from Sf9 cells infected with Bac-inCap6; and (E) AAV1 Cap proteins expressed from Sf9 cells infected with Bac-inCap1.

To express the Rep proteins, Sf9 cells were infected at a multiplicity of infection (m.o.i.) of 1 for 3 days at 28° C. and harvested by centrifugation at 2,000 rpm for 15 min. The cell pellets were lysed in NuPAGE® LDS Sample Buffer (Invitrogen, Carlsbad, Calif.), boiled for 5 min, sonicated for 10 seconds. The lysates were subjected to SDS-polyacrylamide gel electrophoresis (SDS-PAGE). Proteins were transferred onto PVDF membrane and the Rep78 and Rep52 were detected by monoclonal antibody clone 303.9 (American Research Products; San Jose, Calif.). The results presented in FIG. 9A show that both Rep78 and Rep52 were expressed, indicating that the artificial intron was successfully spliced out to give rise to a full length mRNA that was translated into Rep78 protein. The results further indicate that the polh promoter located inside the intron was functional and full length mRNA coding for Rep52 was transcribed and translated into Rep52 protein.

Example 2

This example demonstrates that a single AAV2 Cap coding sequence comprising the artificial intron comprising the polh promoter can express VP1, VP2, and VP3 proteins.

The ORF located at the right side of the wild-type AAV genome codes for three overlapping capsid proteins, VP1, VP2, and VP3. In mammalian cells, these capsid proteins are synthesized from two spliced mRNAs arising from the p40 promoter. One message is translated into VP1, while another transcript encodes VP2 and VP3. The naturally occurring initiation codon for VP2 is ACG, which is poorly utilized, resulting in ribosome scanning through to the VP3 initiation codon (AUG). The alternate usage of two splice acceptor sites and the poor utilization of ACG initiation codon for VP2 are responsible for the stoichiometry of VP1, VP2, and VP3 in AAV2-infected mammalian cells and mirrors the protein ratio in the capsids, 1:1:10. The AAV cap intron is not spliced in insect cells.

Figure 10:
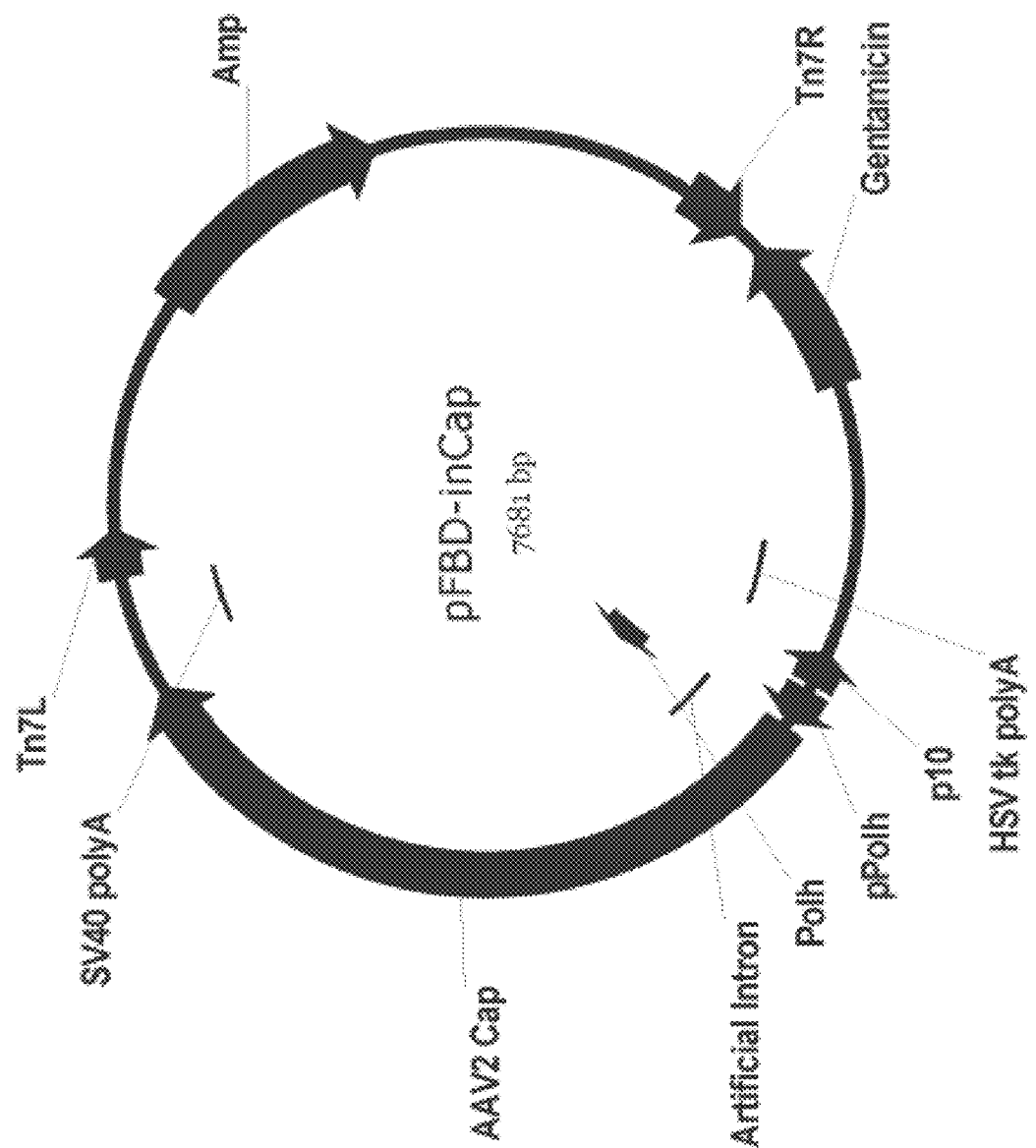
FIG. 10 illustrates a genetic map of a recombinant vector comprising AAV2 Cap coding sequence and an artificial intron comprising polyhedrin (polh) promoter. This vector can be used for the production of AAV2 vectors in insect cells.

In order to express all three capsid proteins from a single coding sequence and preserve the native AUG start codon for VP1 protein, the same artificial intron as described in Example 1 above was used. It was inserted in the Cap coding sequence between nucleotides 2227 and 2228 according to the AAV genome (AF043303) wherein the sequence of nucleotides 2221-2230 is cttccagatt (SEQ ID NO: 26). First the plasmid pAAV-RC was digested with BamHI and EcoNI to isolate the backbone 4969 bp-fragment. The artificial intron was then amplified from pAAV-inRep using primers 5'-GCGCGGATCCTGTTAAGATGGCTGC-CGATGGTTATCTTCCAGGTAAGTACTCC CTATCAGT-GATAGAG-3' (SEQ ID NO: 16) and 5'-ATATCGTCTCGCT-GAAACAATAGGAAGGGAGTGGAT-3' (SEQ ID NO:17). The primer SEQ ID NO: 16 contains a BamHI site and the first 25 nucleotides of VP1 coding sequence (ATGGCTGC-CGATGGTTATCTTCCAG, SEQ ID NO: 27) and the primer SEQ ID NO: 17 contains a BsmBI site. The PCR product was then digested with BamHI and BsmBI. A second PCR fragment was amplified from pAAV-RC using primers 5'-AAT-TCGTCTCGTCAGATTGGCTCGAGGA-CACTCTCTCTGA-3' (SEQ ID NO:18) and 5'-TCCCGGAGCCGTCTTAACAG-3' (SEQ ID NO:19) and digested with restriction enzymes BsmBI and EcoNI. The backbone fragment was ligated with the two PCR fragments to create pAAV-inCap. The entire Cap coding sequence comprising the artificial intron was then digested with BamHI and SnaBI and ligated to the BamHI and HindIII (blunted by Klenow) sites of pFastBacDual plasmid to create plasmid pFBD-inCap (FIG. 10). This plasmid was then used to generate recombinant baculovirus Bac-inCap according to the protocol as described in Example 1. Sf9 cells were infected by Bac-inCap for 3 days at 28° C., harvested and lysed in NuPAGE® LDS Sample Buffer. Proteins were then separated by SDS-PAGE and transferred to PVDF membrane, and probed with a monoclonal antibody directed against AAV capsid proteins (clone B1, American Research Products; San Jose, Calif.). The results shown in FIG. 9B indicate that VP1, VP2, and VP3 proteins were expressed, demonstrating the successful splicing of the artificial intron to form a full length VP1 mRNA that was translated into VP1 protein. The results further demonstrate that the polh promoter located inside the artificial intron was working properly to drive the expression of VP2 and VP3 proteins.

Example 3

This example demonstrates that by using the same design of artificial intron, VP1, VP2, and VP3 proteins can be expressed from AAV8, AAV6, and AAV1 serotypes.

Figure 11:
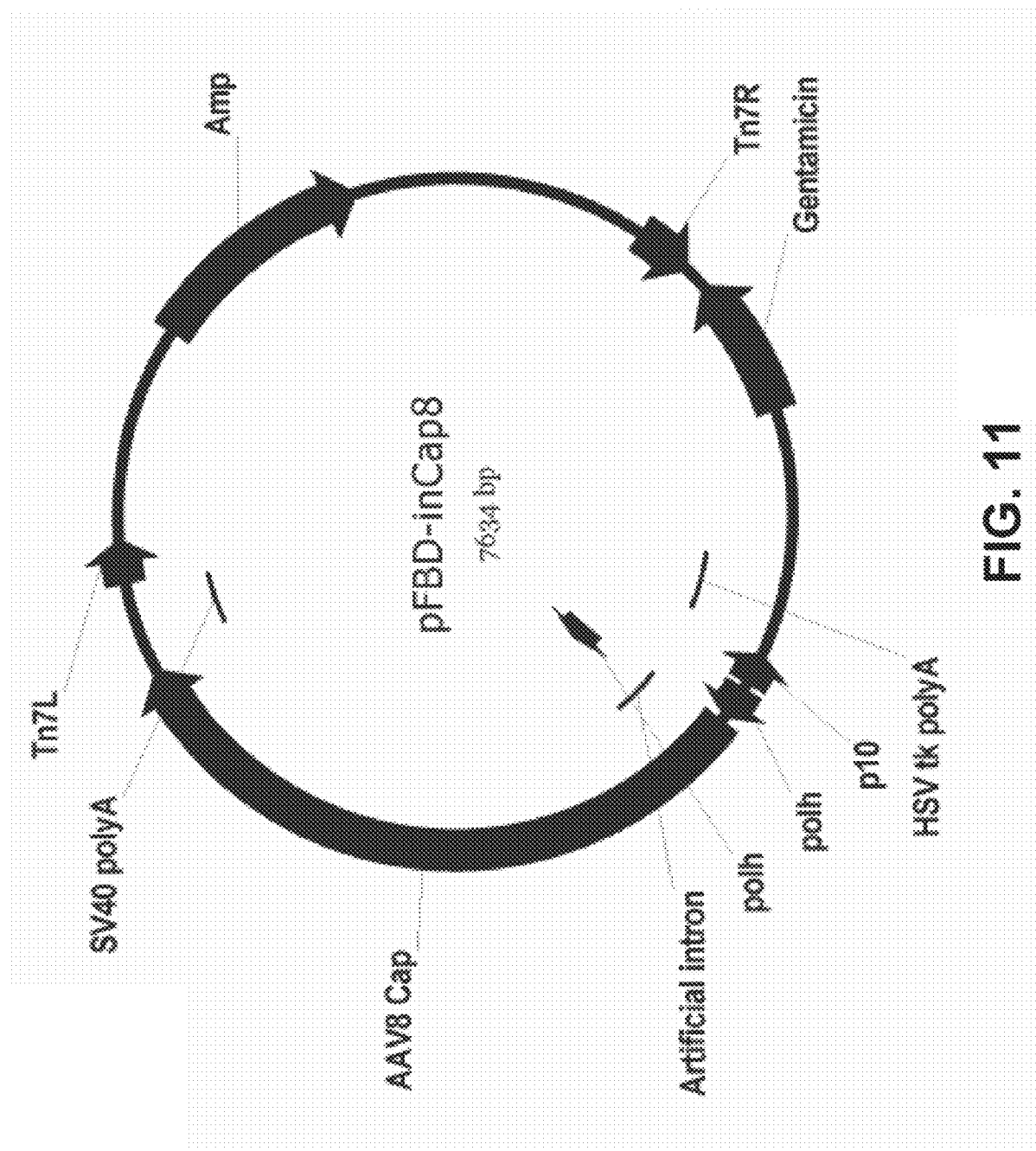
FIG. 11 illustrates a genetic map of a recombinant vector comprising AAV8 Cap coding sequence and an artificial intron comprising polyhedrin (polh) promoter. This vector can be used for the production of AAV8-pseudotyped vectors in insect cells.
Figure 12:
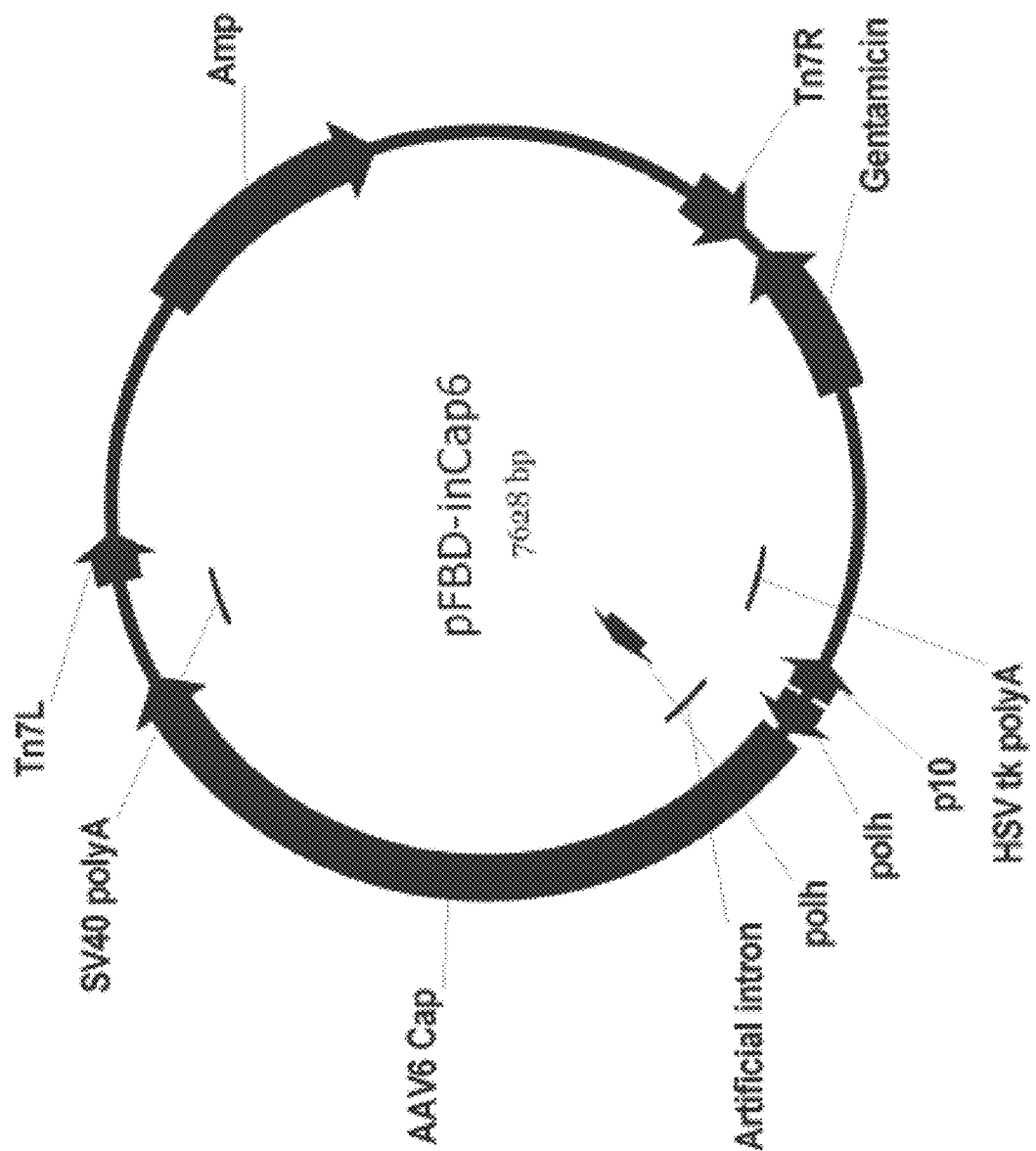
FIG. 12 illustrates a genetic map of a recombinant vector comprising AAV6 Cap coding sequence comprising and an artificial intron comprising polyhedrin (polh) promoter. This vector can be used for the production of AAV6-pseudotyped vectors in insect cells.
Figure 13:
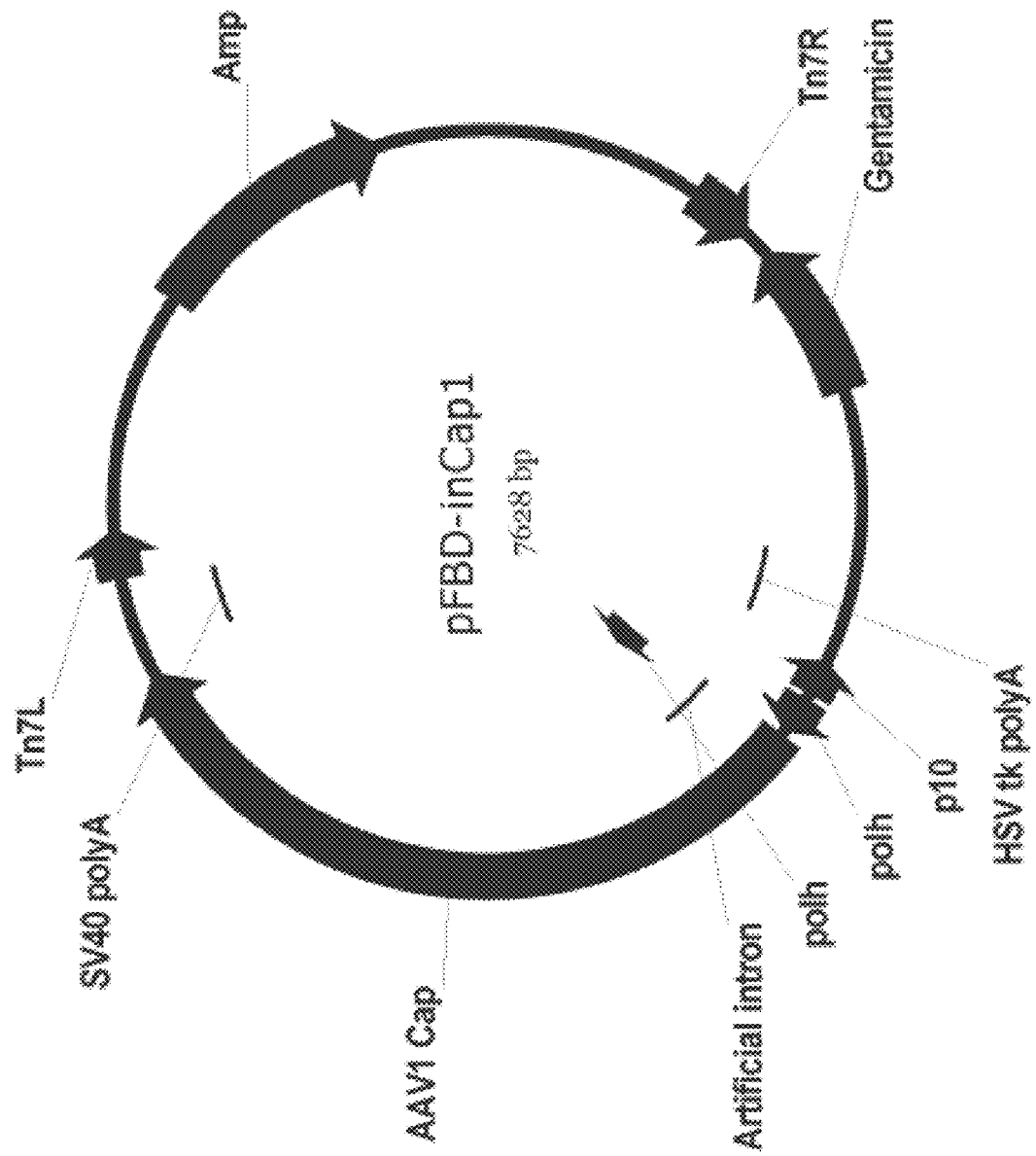
FIG. 13 illustrates a genetic map of a recombinant vector comprising AAV1 Cap coding sequence and an artificial intron comprising a polyhedrin (polh) promoter. This vector can be used for the production of AAV1-pseudotyped vectors in insect cells.

The same artificial intron as used in examples supra was inserted into the Cap coding sequence of AAV serotype 8 between nucleotides 2145 and 2146 (accession no. NC_006261) wherein the nucleotide sequence 2141-2150 is tccagattgg (SEQ ID NO: 28), AAV serotype 6 between nucleotides 2232 and 2233 (accession no. NC_001862), wherein nucleotide sequence 2231-2240 is agattggctc (SEQ ID NO: 32), and AAV serotype 1 between nucleotides 2247 and 2248 (accession no. NC_002077), wherein nucleotide sequence 2241-2250 is cttccagatt (SEQ ID NO: 29, see Example 2). To construct pFBD-inCap8 and pFBD-inCap6, the artificial intron was amplified by PCR from pFBD-inCap using primers 5'-ATGCCCTCAGAGAGGTTGTCCTCGAGC-CAATCTGAAACAAT-3' (SEQ ID NO:21) and 5'-CCCGG-TACCGCATGCTATGC-3' (SEQ ID NO:22). The amplification product was digested with EcoNI and SphI, and the digested product was ligated to the EcoNI and SphI sites of pFBD-Cap8 and pFBD-Cap6 to create pFBD-inCap8 (FIG. 11) and pFBD-inCap6 (FIG. 12) respectively. To clone the artificial intron into the Cap coding sequence of AAV1, pFBD-inCap8 was digested with EcoNI and XbaI to remove the Cap coding sequence of AAV8. The Cap coding sequence of AAV1 was PCR amplified from an AAV 1 plasmid using primers 5'-GATTGGCTCGAGGACAACCTCTCTG-3' (SEQ ID NO:23) and 5'-GGATCCTCTAGAGTCGAC-CGCTTACAGGGGACGGGTAAGGT-3' (SEQ ID NO:24). The EcoNI and XbaI digested PCR fragment was ligated to the EcoNI and XbaI digested pFBD-inCap8 to create pFBD-inCap1 (FIG. 13). Recombinant baculoviruses Bac-inCap8, Bac-inCap6, and Bac-inCap1 were generated according to the manufacturer's protocol as described in example 1. Sf9 cells were infected by Bac-inCap8, Bac-inCap6, and BacinCap1 respectively for 3 days at 28° C., harvested and lysed in NuPAGE® LDS Sample Buffer. Proteins were separated by SDS-PAGE and transferred to PVDF membrane. The VP1, VP2, and VP3 proteins were detected by monoclonal antibody B1 clone (American Research Products; San Jose, Calif.). The results, shown in FIG. 9, indicate that VP1, VP2, and VP3 proteins were successfully expressed from all the serotypes tested, demonstrating the successful splicing of the artificial intron to form a full length VP1 mRNA that was translated into VP1 proteins. These results further demonstrate that the polh promoter inside the artificial intron was working properly in all serotypes tested to drive the expression of VP2 and VP3 proteins.

Example 4

This example demonstrates that rAAV can be produced in insect cells by using the AAV Rep and Cap coding sequences, each comprising an artificial intron.

In these experiments, Sf9 cells were grown at 28° C. to about $10^7$ cells/ml in SF900 II SFM media containing 100 units/ml of penicillin and 100 µg/ml streptomycin, and diluted to about $5 \times 10^6$ cells/ml prior to infection. Triple infection was employed to produce rAAV. A m.o.i. of 1 of each Bac-inRep, Bac-GFP (or Bac-RFP), and Bac-inCap was used to infect the Sf9 cells at 28° C. for 3 days to produce AAV type 2 vectors. For AAV type 1, 6, and 8 vector production, Bac-inCap was simply substituted by Bac-inCap1, Bac-inCap6, and Bac-inCap8, respectively in the triple infection. After 3 days of infection, cell pellets were collected by centrifugation at 2,000 rpm for 15 min in a tabletop centrifuge. The cell pellets were lysed in lysis buffer as described by Urabe et al., Hum Gene Ther. 1; 13(16):1935-43 (2002) and cellular nucleic acids (DNA and RNA) were digested by benzonase (Sigma, St. Louis, Mo.). The cell lysates were cleared by centrifugation at 8,000 rpm for 30 min in an Avanti J-25 centrifuge (Backman, Fullerton, Calif.) and then loaded onto an SW28 centrifuge tube containing 5 ml of 1.55 g/cc, and 10 ml of 1.32 g/cc of CsCl solutions. After centrifugation at 28,000 rpm for about 16 hours at 15° C., the rAAV-containing fraction was collected by puncturing the centrifuge tube using a syringe needle and subjected to a second round of CsCl ultracentrifugation. The rAAV-containing fraction was collected again by puncturing the centrifuge tube using a syringe needle and dialyzed in PBS buffer to remove the salts and detergents. Vector titers were determined by quantitative real-time PCR assay according to manufacturer's protocol (Applied Biosystems, Foster City, Calif.). The results, presented in Table 1, show that high titers of rAAV vectors can be produced in Sf9 cells using the recombinant baculoviruses that carry the Rep and Cap coding sequences comprising the artificial intron, respectively.

TABLE 1

| AAV vector genome yields in Sf9 cells as determined by quantitative RT-PCR | | |
|---|---|---|
| Experiment No. | Serotype & Transgene | Yield (vector genome/liter of Sf9 culture) |
| 1 | AAV2-GFP | $1.56 \times 10^{14}$ |
| 2 | AAV2-RFP | $1.58 \times 10^{14}$ |
| 3 | AAV2-GFP | $9.77 \times 10^{13}$ |
| 4 | AAV6-GFP | $3.53 \times 10^{13}$ |
| 5 | AAV8-GFP | $9.65 \times 10^{13}$ |
| 6 | AAV1-GFP | $4.36 \times 10^{13}$ |
| 7 | AAV1-GFP | $4.47 \times 10^{13}$ |

Example 5

This example demonstrates the production of rAAV in insect cells using the two-vector system.

The Rep and Cap coding sequence each comprising the artificial intron were cloned together using standard cloning techniques into a single baculovirus as shown in FIG. 4. Sf9 cells were grown at 28° C. to $10^7$ cells/ml and diluted to $5 \times 10^6$ cells/ml right before infection. Bac-inRep-inCap and Bac-GFP each at m.o.i. of one were used to infect the cells at 28° C. for 3 days. The cells were harvested and rAAV vectors were purified as described in Example 4. The results, presented in TABLE 2, indicate the successful production of AAV2 vectors using the two-vector system.

TABLE 2

| AAV vector genome yields in Sf9 cells as determined by quantitative RT-PCR | | |
|---|---|---|
| Experiment No. | Serotype & Transgene | Yield (vector genome/liter of Sf9 culture) |
| 1 | AAV2-GFP | $1.33 \times 10^{14}$ |
| 2 | AAV2-GFP | $1.06 \times 10^{14}$ |

Example 6

This example demonstrates that VP1, VP2, and VP3 proteins are properly packaged in virions by using AAV Cap coding sequences comprising the artificial intron.

In these experiments, purified AAV2, AAV6, and AAV8 vectors, each at $10^{10}$ vector genomes, were boiled in NuPAGE® LDS Sample Buffer for 5 min. Proteins were resolved by SDS-PAGE and transferred to PVDF membrane. The VP1, VP2, and VP3 proteins were detected by monoclonal antibody B1 clone as described in Example 2. The results demonstrate that by using the Cap coding sequences comprising the artificial intron, all three capsid proteins can be properly packaged into virions.

Example 7

This example illustrates that AAV vectors produced in the insect cells using the Rep and Cap coding sequences comprising the artificial intron are infectious and can deliver genes to target cells.

In these experiments, AAV2-GFP and AAV6-GFP were used to transduce HepG2 hepatocellular carcinoma cells (American Type Culture Collection, Manassas, Va.) to show the infectivity of the vectors produced in insect cells. HepG2 cells were grown at 37° C. in MEM medium (ATCC) supplemented with 10% fetal bovine serum (Hyclone, Logan, Utah) and 100 units/ml of penicillin and 100 µg/ml of streptomycin (Invitrogen, Carlsbad, Calif.). HepG2 cells at $1.5 \times 10^5$ cells/well were seeded in 24-well plate and grown overnight at 37° C. in a $CO_2$ incubator. AAV vectors were diluted to $1.2 \times 10^9$ vg/ml, $1.2 \times 10^8$ vg/ml, $1.2 \times 10^7$ vg/ml, and $1.2 \times 10^6$ vg/ml in the culture medium without serum but containing 20 µM of etoposide (A.G. Scientific, Inc., San Diego, Calif.). Old media were removed from the cells and 500 µl of diluted AAV vectors were added to each well. Two days after transduction, GFP expressing cells were scored and photographed. The results show that HepG2 cells were efficiently transduced both by AAV2-GFP and AAV6-GFP vectors.

Example 8

This example illustrates that nucleic acid sequences of the present teachings comprising Rep- or Cap-encoding sequences and an artificial intron are stable in a baculovirus.

To demonstrate the stability of baculoviruses comprising the Rep and Cap coding sequences respectively, the baculoviruses were plaque purified and subsequently passaged for 5 times, and Rep and Cap protein expression was assayed. The plaque purification was performed as follows: Sf9 cells at $1\times10^6$ cells/well were seeded in 6-well plate and incubated at 28° C. for 30 min. The baculoviruses were diluted to 100, 50, and 25 pfu/100 µl. Old media were removed from the cells and the diluted baculoviruses were added to infect the cells for 20 min at 28° C. Agarose in DPBS at 1% was melted, cool to 37° C., and mixed with 1 volume of SF900II SFM at 37° C., and 1.5 ml of the agarose-SF900II SFM overlay was added to each well. When the agarose solidified, 1.5 ml of SF900II SFM was added to each well and the plates were incubated at 28° C. for 6 days to let plaques form. By the end of incubation, 6 plaques from Bac-inCap and 12 plaques from Bac-inRep were picked and transferred to microfuge tubes containing 500 µl SF900II SFM media. Sf9 cells in 6-well plates were infected with 100 µl of each plaque for 4 days. The cells were collected for Western blot analysis and the supernatants were collected and 3 µl of the supernatants were used to infect Sf9 cells in 6-well plates. This procedure was repeated for 4 more times until passage 5. The results show that all the plaques picked through 5 passages express the Rep78 and Rep52 or the VP1, VP2, and VP3 proteins as expected, with no apparent loss of protein expression.

Example 9

This example demonstrates expression in an insect cell of multiple SV40 VP proteins from a single expression cassette comprising multiple introns.

Simian virus 40 (SV40) is a double-stranded DNA virus with a covalently closed circular genome of 5.2 kb, and has been sequenced in its entirety (Fiers, W., et al., Nature 273: 113-120, 1978). The sequence is available on the internet at http://www.ncbi.nlm.nih.gov/entrez/viewer.fcgi?db=nuccore&id=9628421, accession no. NC_001669. In mammalian cells, its three capsid proteins, VP1, VP2, and VP3 are all transcribed from the same SV40 promoter and expression of these VP proteins is controlled by mechanism of intron splicing. The VP3 protein is a truncated form of the VP2 protein and the 5' portion the sequence encoding the VP1 protein is overlapping with the 3' portion of VP2 and VP3 but does not share the same ORF.

Figure 14:
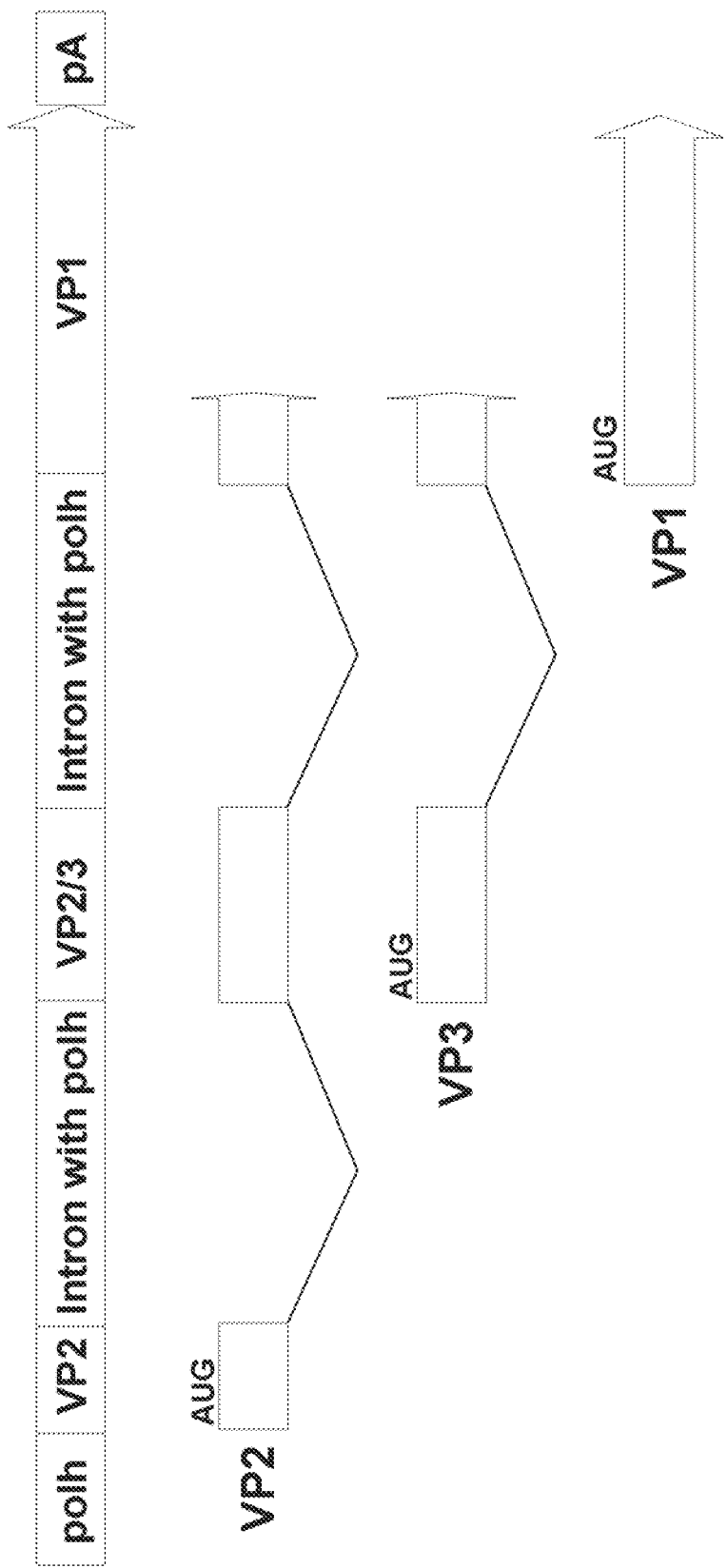
FIG. 14 illustrates a genetic and transcriptional map of recombinant baculovirus expressing all three SV40 VP proteins within a single expression cassette. Mature VP2 mRNA is formed when both the first and second introns are removed through splicing and mature VP3 mRNA is formed when the second intron is removed through splicing. The VP1 mRNA is transcribed from the promoter located inside the second intron.

Artificial introns can be used to express SV40 capsid proteins in insect cells. To drive VP3 expression, an artificial intron comprising a polh promoter is inserted into the SV40 genome between nucleotides 913 and 914 wherein the sequence of nucleotides 911-920 is caggaatggc (SEQ ID NO: 30). To drive VP1 expression, an artificial intron comprising the same polh promoter is inserted between nucleotides 1462 and 1463 wherein the sequence of nucleotides 1461-1470 is aggcctgtac (SEQ ID NO: 31). The VP2 protein is expressed from the polh promoter operably linked to the VP2 gene (FIG. 14).

All publications and patent applications cited in this specification are herein incorporated by reference as if each individual publication or patent application were specifically and individually indicated to be incorporated by reference. Although the foregoing teachings have been described in some detail by way of illustration and example for purposes of clarity of understanding, it will be readily apparent to those of ordinary skill in the art in light of the teachings that certain changes and modifications may be made thereto without departing from the spirit or scope of the appended claims.

REFERENCES

1. Berns, K. I., "*Parvoviridae*: The Viruses and Their Replication," Chapter 69 in Fields Virology (3d Ed. 1996).
2. Choi et al., Curr. Gene Ther., June; 5(3):299-310 (2005).
3. Tratschin et al., Mol. Cell Biol., 5(11):3251-3260 (1985).
4. Grimm et al., Hum. Gene Ther., 10(15):2445-2450 (1999).
5. Jennings et al., Arthritis Res, 3:1 (2001).
6. Davidson et al., Proc. Natl. Acad. Sci. USA, 97(7):3428-3432 (2000).
7. Urabi et al., J Virol., 80(4):1874-85 (2006).
8. Kohlbrenner et al., Mol. Ther., 12(6):1217-25 (2005).
9. Chao et al., Mol. Ther. 2:619 (2000).
10. Chiorini et al., J. Virol. 73:1309 (1999).
11. Xiao et al., J. Virol. 73:3994 (1999).
12. Muramatsu et al., Virology 221:208 (1996).
13. Chiorini et al., J. Vir. 71: 6823-33 (1997).
14. Srivastava et al., J. Vir. 45:555-64 (1983).
15. Chiorini et al., J. Vir. 73:1309-1319 (1999).
16. Rutledge et al., J. Vir. 72:309-319 (1998).
17. Wu et al., J. Vir. 74: 8635-47 (2000).
18. Samulski et al., J. Vir. 63:3822-8 (1989).
19. Kajigaya et al., Proc. Nat'l. Acad. Sci. USA 88: 4646-50 (1991).
20. Ruffing et al., J. Vir. 66:6922-30 (1992)
21. Kimbauer et al., Vir. 219:37-44 (1996).
22. Zhao et al., Vir. 272:382-93 (2000).
23. Chisholm and Henner, J. Virol., 62(9):3193-3200 (1988).

U.S. PATENT DOCUMENTS

| | | |
|---|---|---|
| 5,387,484 A | February 1995 | Doany |
| 5,688,676 A | November 1997 | Zhou et al. |
| 5,691,176 A | November 1997 | Lebkowski et al. |
| 5,741,683 A | April 1998 | Russell et al. |
| 6,204,059 B1 | March 2001 | Samulski et al. |
| 2002/0081721 A1 | June 2002 | Allen et al. |
| 6,723,551 B2 | April 2004 | Kotin, et al |
| 2006/0166363 A1 | July 2006 | Zolotukhin et al. |

What is claimed is:

1. A nucleic acid cassette for expressing in an insect cell a plurality of polypeptides encoded by a parvovirus capsid gene, the cassette comprising in 5' to 3' order:
   (i) a first insect cell operable promoter linked operably to a 5' portion of a first ORF of the parvovirus capsid gene, the first ORF comprising a translation initiation codon,
   (ii) an intron comprising a second insect cell operable promoter, the second promoter operably linked to a 5' portion of an at least one additional ORF of a parvovirus capsid gene, wherein the at least one additional ORF comprises at least one additional translation initiation codon and overlaps with the 3' portion of the first ORF.

2. A nucleic acid cassette in accordance with claim 1, wherein the first ORF is a VP1 ORF and the at least one additional ORF is a VP2/VP3 ORF.

3. A nucleic acid cassette for expressing in an insect cell a plurality of polypeptides encoded by a parvovirus Rep gene, the cassette comprising in 5' to 3' order:
   (i) a first insect cell operable promoter linked operably to a 5' portion of a first ORF of the parvovirus Rep gene, the first ORF comprising a translation initiation codon,
   (ii) an intron comprising a second insect cell operable promoter, the second promoter operably linked to a 5' portion of an at least one additional ORF of a parvovirus Rep gene, wherein the at least one additional ORF comprises at least one additional translation initiation codon and overlaps with the 3' portion of the first ORF.

4. A nucleic acid cassette for expressing in an insect cell a plurality of polypeptides encoded by a polyomavirus gene, the cassette comprising in 5' to 3' order:
   (i) a first insect cell operable promoter linked operably to a 5' portion of a first ORF of a polyomavirus capsid gene, the first ORF comprising a translation initiation codon,
   (ii) an intron comprising a second insect cell operable promoter, the second promoter operably linked to a 5' portion of an at least one additional ORF of a polyomavirus capsid gene, wherein the at least one additional ORF comprises at least one additional translation initiation codon and overlaps with the 3' portion of the first ORF.

5. A nucleic acid cassette in accordance with claim 1, 3 or 4, further comprising a polyadenylation signal situated 3' to the additional ORF in (ii).

6. A nucleic acid cassette in accordance with claim 1, 3 or 4, wherein each of the first insect cell-operable promoter and the second insect cell-operable promoter is independently selected from the group consisting of a p10 promoter and a polh promoter.

7. A nucleic acid cassette in accordance with claim 3, wherein the first ORF is a Rep 78/68 ORF and the at least one additional ORF is a Rep 52/40 ORF.

8. A nucleic acid cassette in accordance with claim 1, 3 or 4, wherein the first promoter is a p10 promoter and the second promoter is a polh promoter.

9. A nucleic acid cassette in accordance with claim 1, 3 or 4, wherein the first promoter is a first polh promoter and the second promoter is a second polh promoter.

10. A vector comprising the nucleic acid cassette of claim 1, 3 or 4.

11. A vector in accordance with claim 10, wherein the vector is selected from the group consisting of a plasmid, a virus and a combination thereof.

12. An isolated insect cell comprising the nucleic acid cassette of claim 1, 3 or 4.

13. An isolated insect cell comprising a first nucleic acid cassette of claim 1 and a
   second nucleic acid cassette, wherein the first nucleic acid cassette comprises a Cap gene comprising a VP1 ORF and a VP2/VP3 ORF and the second nucleic acid cassette comprises:
   (i) a first insect cell operable promoter linked operably to a 5' portion of a first ORF of the parvovirus Rep gene, the first ORF comprising a translation initiation codon,
   (ii) an intron comprising a second insect cell operable promoter, the second promoter operably linked to a 5' portion of an at least one additional ORF of a parvovirus Rep gene, wherein the at least one additional ORF comprises at least one additional translation initiation codon and overlaps with the 3' portion of the first ORF.

14. An isolated insect cell in accordance with claim 13, further comprising an additional nucleic acid cassette, the additional cassette comprising, in 5' to 3' order:
   a first inverted terminal repeat (ITR) of an adeno-associated virus;
   a mammalian cell-operable promoter;
   a transgene;
   a polyadenylation signal; and
   a second ITR of an AAV.

15. An insect cell in accordance with claim 14, wherein the transgene is a reporter gene encoding a polypeptide selected from the group consisting of a chloramphenicol acetyl transferase, a β-galactosidase, a β-glucuronidase, a renilla luciferase, a firefly luciferase, a green fluorescent protein (GFP), a red fluorescent protein (RFP) and an alkaline phosphatase.

16. An insect cell in accordance with claim 14, wherein the transgene comprises an ORF encoding a polypeptide selected from the group consisting of a polypeptide hormone, an interferon, a blood clotting factor, a vaccine and an erythropoietin.

17. An insect cell in accordance with claim 12, wherein the nucleic acid cassette is integrated into the genome of the insect cell.

18. An insect cell in accordance with claim 14, wherein at least one of the nucleic acid cassette and the additional nucleic acid cassette is integrated into the genome of the insect cell.

19. An insect cell in accordance with claim 12, wherein the cell is selected from the group consisting of a *Trichoplusia ni* BTI-Tn-5B1-4 cell, a *Spodoptera frugiperda* Sf9 cell and a *Spodoptera frugiperda* Sf21 cell.

20. A cell culture comprising:
   a plurality of insect cells of claim 12;
   and a culture medium.

21. A cell culture comprising:
   a plurality of insect cells of claim 14; and
   a culture medium comprising at least $10^{13}$ AAV genomes/liter.

22. A cell culture in accordance with claim 21, wherein the culture medium comprising at least $10^{13}$ AAV genomes/liter is a culture medium comprising at least $10^{14}$ AAV genomes/liter.

23. A nucleic acid comprising the cassette of claim 5, further comprising a second cassette, the second cassette comprising, in 5' to 3' order:
   a second polyadenylation signal;
   a 3' portion of a second gene comprising overlapping ORFs;
   a second intron comprising a third insect-operable promoter;
   a 5' portion of the second gene; and
   a fourth insect operable promoter.

24. A nucleic acid in accordance with claim 23, wherein the second cassette is in an anti-sense orientation relative to the first cassette.

25. A nucleic acid in accordance with claim 23, wherein the second cassette is in a sense orientation relative to the first cassette.

26. A nucleic acid in accordance with claim 23, wherein the first cassette comprises an AAV Rep gene comprising a Rep 78/68 ORF and a Rep 52/40 ORF and the second cassette comprises an AAV Cap gene comprising a VP1 ORF and a VP2/VP3 ORF.

* * * * *

SEQUENCE LISTING

<160> NUMBER OF SEQ ID NOS: 31

<210> SEQ ID NO 1
<211> LENGTH: 229
<212> TYPE: DNA
<213> ORGANISM: Artificial Sequence

```
<220> FEATURE:
<223> OTHER INFORMATION: Synthetic

<400> SEQUENCE: 1
gtaagtactc cctatcagtg atagagatct atcatggaga taattaaaat gataaccatc    60
tcgcaaataa ataagtattt tactgttttc gtaacagttt tgtaataaaa aaacctataa   120
atattccgga ttattcatac cgtcccacca tcgggcgcga agggggagac ctgtagtcag   180
agccccgggg cagcacacac tgacatccac tcccttccta ttgtttcag               229

<210> SEQ ID NO 2
<211> LENGTH: 59
<212> TYPE: DNA
<213> ORGANISM: Artificial Sequence
<220> FEATURE:
<223> OTHER INFORMATION: Synthetic

<400> SEQUENCE: 2
cagtgggcgt ggactaatat ggaacagtat ttaaggtaag tactccctat cagtgatag     59

<210> SEQ ID NO 3
<211> LENGTH: 60
<212> TYPE: DNA
<213> ORGANISM: Artificial Sequence
<220> FEATURE:
<223> OTHER INFORMATION: Synthetic

<400> SEQUENCE: 3
agatctatca tggagataat taaaatgata accatctcgc aaataaataa gtattttact    60

<210> SEQ ID NO 4
<211> LENGTH: 60
<212> TYPE: DNA
<213> ORGANISM: Artificial Sequence
<220> FEATURE:
<223> OTHER INFORMATION: Synthetic

<400> SEQUENCE: 4
gttttcgtaa cagttttgta ataaaaaaac ctataaatat tccggattat tcataccgtc    60

<210> SEQ ID NO 5
<211> LENGTH: 60
<212> TYPE: DNA
<213> ORGANISM: Artificial Sequence
<220> FEATURE:
<223> OTHER INFORMATION: Synthetic

<400> SEQUENCE: 5
ccaccatcgg gcgcgaaggg ggagacctgt agtcagagcc cccgggcagc acacactgac    60

<210> SEQ ID NO 6
<211> LENGTH: 60
<212> TYPE: DNA
<213> ORGANISM: Artificial Sequence
<220> FEATURE:
<223> OTHER INFORMATION: Synthetic

<400> SEQUENCE: 6
atccactccc ttcctattgt ttcagcgcct gtttgaatct cacggagcgt aaacggttgg    60

<210> SEQ ID NO 7
<211> LENGTH: 20
<212> TYPE: DNA
<213> ORGANISM: Artificial Sequence
<220> FEATURE:
```

```
<223> OTHER INFORMATION: Synthetic

<400> SEQUENCE: 7
tggcgcagca tctgacgcac                                                  20

<210> SEQ ID NO 8
<211> LENGTH: 50
<212> TYPE: DNA
<213> ORGANISM: Artificial Sequence
<220> FEATURE:
<223> OTHER INFORMATION: Synthetic

<400> SEQUENCE: 8
gcgtcagatg ctgcgccacc aaccgtttac gctccgtgag attcaaacag                 50

<210> SEQ ID NO 9
<211> LENGTH: 60
<212> TYPE: DNA
<213> ORGANISM: Artificial Sequence
<220> FEATURE:
<223> OTHER INFORMATION: Synthetic

<400> SEQUENCE: 9
gcgctgaaac aataggaagg gagtggatgt cagtgtgtgc tgcccggggg ctctgactac      60

<210> SEQ ID NO 10
<211> LENGTH: 60
<212> TYPE: DNA
<213> ORGANISM: Artificial Sequence
<220> FEATURE:
<223> OTHER INFORMATION: Synthetic

<400> SEQUENCE: 10
aggtctcccc cttcgcgccc gatggtggga cggtatgaat aatccggaat atttataggt      60

<210> SEQ ID NO 11
<211> LENGTH: 60
<212> TYPE: DNA
<213> ORGANISM: Artificial Sequence
<220> FEATURE:
<223> OTHER INFORMATION: Synthetic

<400> SEQUENCE: 11 tttttttatta caaaactgtt acgaaaacag taaaatactt atttatttgc gagatggtta    60

<210> SEQ ID NO 12
<211> LENGTH: 60
<212> TYPE: DNA
<213> ORGANISM: Artificial Sequence
<220> FEATURE:
<223> OTHER INFORMATION: Synthetic

<400> SEQUENCE: 12
tcattttaat tatctccatg atagatctct atcactgata gggagtactt accttaaata     60

<210> SEQ ID NO 13
<211> LENGTH: 32
<212> TYPE: DNA
<213> ORGANISM: Artificial Sequence
<220> FEATURE:
<223> OTHER INFORMATION: Synthetic

<400> SEQUENCE: 13
ctgttccata ttagtccacg cccactggag ct                                   32
```

<210> SEQ ID NO 14
<211> LENGTH: 35
<212> TYPE: DNA
<213> ORGANISM: Artificial Sequence
<220> FEATURE:
<223> OTHER INFORMATION: Synthetic

<400> SEQUENCE: 14
gtgtgtatac ccgccatgcc ggggttttac gagat                               35

<210> SEQ ID NO 15
<211> LENGTH: 35
<212> TYPE: DNA
<213> ORGANISM: Artificial Sequence
<220> FEATURE:
<223> OTHER INFORMATION: Synthetic

<400> SEQUENCE: 15
gcgcgcatgc tccttcagag agagtgtcct cgagc                               35

<210> SEQ ID NO 16
<211> LENGTH: 68
<212> TYPE: DNA
<213> ORGANISM: Artificial Sequence
<220> FEATURE:
<223> OTHER INFORMATION: Synthetic

<400> SEQUENCE: 16
gcgcggatcc tgttaagatg gctgccgatg gttatcttcc aggtaagtac tccctatcag    60
tgatagag                                                             68

<210> SEQ ID NO 17
<211> LENGTH: 36
<212> TYPE: DNA
<213> ORGANISM: Artificial Sequence
<220> FEATURE:
<223> OTHER INFORMATION: Synthetic

<400> SEQUENCE: 17
atatcgtctc gctgaaacaa taggaaggga gtggat                              36

<210> SEQ ID NO 18
<211> LENGTH: 40
<212> TYPE: DNA
<213> ORGANISM: Artificial Sequence
<220> FEATURE:
<223> OTHER INFORMATION: Synthetic

<400> SEQUENCE: 18
aattcgtctc gtcagattgg ctcgaggaca ctctctctga                          40

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
tcccggagcc gtcttaacag                                                20

<210> SEQ ID NO 20
<211> LENGTH: 129
<212> TYPE: DNA
<213> ORGANISM: Artificial Sequence
<220> FEATURE:

<223> OTHER INFORMATION: Synthetic

<400> SEQUENCE: 20
atcatggaga taattaaaat gataaccatc tcgcaaataa ataagtattt tactgttttc    60
gtaacagttt tgtaataaaa aaacctataa atattccgga ttattcatac cgtcccacca   120
tcgggcgcg                                                           129

<210> SEQ ID NO 21
<211> LENGTH: 41
<212> TYPE: DNA
<213> ORGANISM: Artificial Sequence
<220> FEATURE:
<223> OTHER INFORMATION: Synthetic

<400> SEQUENCE: 21
atgccctcag agaggttgtc ctcgagccaa tctgaaacaa t                        41

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
cccggtaccg catgctatgc                                                20

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23
gattggctcg aggacaacct ctctg                                          25

<210> SEQ ID NO 24
<211> LENGTH: 41
<212> TYPE: DNA
<213> ORGANISM: Artificial Sequence
<220> FEATURE:
<223> OTHER INFORMATION: Synthetic

<400> SEQUENCE: 24
ggatcctcta gagtcgaccg cttacagggg acgggtaagg t                        41

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
agtatttaag cgcctgtttg                                                20

<210> SEQ ID NO 26
<211> LENGTH: 10
<212> TYPE: DNA
<213> ORGANISM: Artificial Sequence
<220> FEATURE:
<223> OTHER INFORMATION: Synthetic

<400> SEQUENCE: 26

```
cttccagatt                                                              10

<210> SEQ ID NO 27
<211> LENGTH: 25
<212> TYPE: DNA
<213> ORGANISM: Artificial Sequence
<220> FEATURE:
<223> OTHER INFORMATION: Synthetic

<400> SEQUENCE: 27
atggctgccg atggttatct tccag                                             25

<210> SEQ ID NO 28
<211> LENGTH: 10
<212> TYPE: DNA
<213> ORGANISM: Artificial Sequence
<220> FEATURE:
<223> OTHER INFORMATION: Synthetic

<400> SEQUENCE: 28
tccagattgg                                                              10

<210> SEQ ID NO 29
<211> LENGTH: 10
<212> TYPE: DNA
<213> ORGANISM: Artificial Sequence
<220> FEATURE:
<223> OTHER INFORMATION: Synthetic

<400> SEQUENCE: 29
cttccagatt                                                              10

<210> SEQ ID NO 30
<211> LENGTH: 10
<212> TYPE: DNA
<213> ORGANISM: Artificial Sequence
<220> FEATURE:
<223> OTHER INFORMATION: Synthetic

<400> SEQUENCE: 30
caggaatggc                                                              10

<210> SEQ ID NO 31
<211> LENGTH: 10
<212> TYPE: DNA
<213> ORGANISM: Artificial Sequence
<220> FEATURE:
<223> OTHER INFORMATION: Synthetic

<400> SEQUENCE: 31
aggcctgtac                                                              10
```